United States Patent
Hoener et al.

(10) Patent No.: US 10,273,217 B2
(45) Date of Patent: Apr. 30, 2019

(54) TRIAZOLE DERIVATIVES

(71) Applicant: Hoffmann-La Roche Inc., Little Falls, NJ (US)

(72) Inventors: Marius Hoener, Basel (CH); Juergen Wichmann, Steinen (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/938,587

(22) Filed: Mar. 28, 2018

(65) Prior Publication Data
US 2018/0237401 A1 Aug. 23, 2018

Related U.S. Application Data

(63) Continuation of application No. PCT/EP2016/073589, filed on Oct. 4, 2016.

(30) Foreign Application Priority Data

Oct. 6, 2015 (EP) ...................................... 15188567

(51) Int. Cl.
| | | |
|---|---|---|
| C07D 249/08 | (2006.01) | |
| C07D 409/12 | (2006.01) | |
| C07D 249/02 | (2006.01) | |
| A61P 25/18 | (2006.01) | |

(52) U.S. Cl.
CPC ............ *C07D 249/08* (2013.01); *A61P 25/18* (2018.01); *C07D 249/02* (2013.01); *C07D 409/12* (2013.01)

(58) Field of Classification Search
CPC .................................................. C07D 240/08
See application file for complete search history.

(56) References Cited

U.S. PATENT DOCUMENTS

| 10,005,736 B1 | 6/2018 | Hoener et al. |
|---|---|---|
| 2009/0163499 A1 | 6/2009 | Chen et al. |

FOREIGN PATENT DOCUMENTS

| JP | 2006-151954 A | 6/2006 |
|---|---|---|
| JP | 2010-540585 A | 12/2010 |
| JP | 2011-528658 A | 11/2011 |
| WO | 2007/042545 A1 | 4/2007 |
| WO | 2008/000645 A1 | 1/2008 |
| WO | 2009/043780 A1 | 4/2009 |
| WO | 2009/077366 A1 | 6/2009 |
| WO | 2009/077367 A1 | 6/2009 |
| WO | 2010/009062 A1 | 1/2010 |
| WO | 2010/051188 A1 | 5/2010 |
| WO | 2016/169902 A1 | 10/2016 |
| WO | 2016/193235 | 12/2016 |
| WO | 2017/072083 | 5/2017 |

OTHER PUBLICATIONS

ISR of PCT/EP2016/058594 (Dated Jun. 24, 2016)
Greenfield Alexander et al., "Synthesis and biological activities of aryl-ether-, biaryl-, and fluorene-aspartic acid and diaminopropionic acid analogs as potent inhibitors of the high-affinity glutamate transporter EAAT-2" Biorganic & Medicinal Chemistry Letters 15(22):4985-4988 (Nov. 14, 2005).
ISR and Written Opinion of PCT/EP2016/062204 (dated Jul. 27, 2016).
Bridges Richard J. et al., "The excitatory amino acid transporters: pharmacological insights on substrate and inhibitor specificity of the EAAT subtypes" Pharmacology & Therapeutics 107(3):271-285 (Sep. 1, 2005).
Product Sheets R&D Systems, Human FGF R3 (IIIb) Antibody, Monoclonal Mouse IgG\\\subscript:1\\\ Clone #133111, MAB765 (downloaded Aug. 31, 2011).

(Continued)

*Primary Examiner* — Laura L Stockton
(74) *Attorney, Agent, or Firm* — Mark D. Kafka; Genentech, Inc.

(57) ABSTRACT

The present invention relates to compounds of formula I

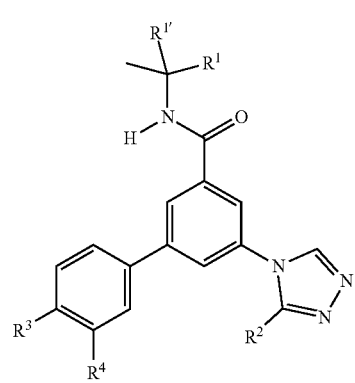

wherein
$R^{1'}$ is $CH_3$
$R^1$ is methyl, ethyl, $CF_3$, $CH_2OH$, cyclopropyl or cyano, or $R^{1'}$ and $R^1$ may form together a 1,1-dioxo-tetrahydro-thiophen-3-yl ring;
$R^2$ is hydrogen, methyl, ethyl, isopropyl, tert-butyl, cyclopropyl, hydroxymethyl, or 2-propyl-2-ol;
$R^3$ is Cl, F, $CF_3$, cyano, methyl, methoxy, isopropyl, or cyclopropyl;
$R^4$ is hydrogen, methyl, F or Cl;
or to a pharmaceutically acceptable salt or acid addition salt, to a racemic mixture, or to its corresponding enantiomer and/or optical isomer and/or stereoisomer thereof.

The compounds of formula I may be used in the treatment of psychiatric disorders such as schizophrenia, bipolar disorder, obsessive-compulsive disorder or autism spectrum disorder.

17 Claims, No Drawings

(56) References Cited

OTHER PUBLICATIONS

Mavencamp Terri L. et al., "Synthesis and preliminary pharmacological evaluation of novel derivatives of L-β-threo-benzylaspartate as inhibitors of the neuronal glutamate transporter EAAT3" Bioorganic & Medicinal Chemistry 16(16):7740-7748 (Aug. 15, 2008).

Jing et al., "GFRα-2 and GFRα-3 Are Two New Receptors for Ligands of the GDNF Family" Journal of Biological Chemistry 272(52):33111-33117 (Dec. 26, 1997).

Jarzylo et al., "Parasynaptic NMDA Receptor Signaling Couples Neuronal Glutamate Transporter Function to AMPA Receptor Synaptic Distribution and Stability" The Journal of Neuroscience 32(7):25522563 ( 2012) , pp. 2252-2563.

Andersen J Jensen et al., "Excitatory amino acid transporters: recent insights into molecular mechanisms, novel modes of modulation and new therapeutic possibilities" Current Opinion in Pharmacology 20:116-123 (Feb. 1, 2015).

Bridges et al., "The excitatory amino acid transporters: pharmacological insights on substrate and inhibitor specificity of the EAAT subtypes" Pharmacology & Therapeutics 107:271 285 ( 2005) , pp. 271-285.

Nieoullon et al., "The neuronal excitatory amino acid transporter EAAC1/EAAT3: does it represent a major actor at the brain excitatory synapse?" Journal of Neurochemistry 98:10071018 ( 2006) , pp. 1007-1018.

Scimemi et al., "Neuronal Transporters Regulate Glutamate Clearance, NMDA Receptor Activation, and Synaptic Plasticity in the Hippocampus" The Journal of Neuroscience 29(46):1458114595 ( 2009) , pp. 14581-14595.

ISR of PCT/EP2016/075590 (Date of mailing Jan. 27, 2017).

Wendland et al., "A Haplotype Containing Quantitative Trait Loci for SLC1A1 Gene Expression and Its Association With Obsessive-Compulsive Disorder" Arch Gen Psychiatry 66(4):408416 ( 2009) , pp. 408-416.

Aoyama et al., "Neuronal glutathione deficiency and age-dependent neurodegeneration in the EAAC1 deficient mouse." Nat Neurosci. 9(1):119-26 ( 2006).

ISR of PCT/EP2016/073589 (Completed Nov. 7, 2016).

ISR of PCT/EP2017/051873 (Completed Feb. 27, 2017).

ISR of PCT/EP2017/062512 (Completed Jul. 11, 2017).

TRIAZOLE DERIVATIVES

CROSS-REFERENCE TO RELATED APPLICATIONS

This application is a continuation of, and claims priority to, International Patent Application No. PCT/EP2016/073589, filed on Oct. 4, 2016. This application also claims priority to European Patent Application No. 15188567.0, filed on Oct. 6, 2015.

The present invention relates to compounds of formula I

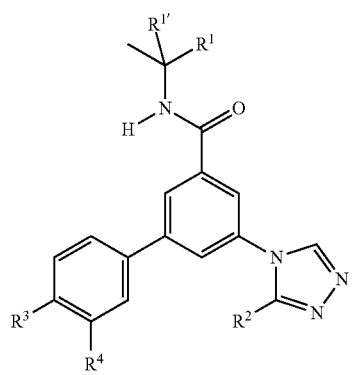

wherein
$R^{1'}$ is $CH_3$
$R^1$ is methyl, ethyl, $CF_3$, $CH_2OH$, cyclopropyl or cyano, or $R^{1'}$ and $R^1$ may form together a 1,1-dioxo-tetrahydro-thiophen-3-yl ring;
$R^2$ is hydrogen, methyl, ethyl, isopropyl, tert-butyl, cyclopropyl, hydroxmethyl, or 2-propyl-2-ol;
$R^3$ is Cl, F, $CF_3$, cyano, methyl, methoxy, isopropyl, or cyclopropyl;
$R^4$ is hydrogen, methyl, F or Cl;
or to a pharmaceutically acceptable salt or acid addition salt, to a racemic mixture, or to its corresponding enantiomer and/or optical isomer and/or stereoisomer thereof.

The compounds of formula I may be used in the treatment of psychiatric disorders such as schizophrenia, bipolar disorder, obsessive-compulsive disorder or autism spectrum disorder.

It has been surprisingly been found that the compounds of general formula I are EAAT3 inhibitors.

The excitatory amino acid transporter 3 (EAAT3), also referred to in human studies as solute carrier family 1, member 1 (systematic gene name: SLC1A1) and in rodents as excitatory amino acid carrier 1 (EAAC1), is a high-affinity anionic amino acid transporter found in neurons throughout the cortex and in the hippocampus, basal ganglia (striatum, thalamus), and the olfactory bulb. EAAT3 functions to buffer local glutamate concentrations at excitatory synapses, for example in the hippocampus, and modulates the differential recruitment of glutamate receptor subtypes at extrasynaptic sites. Furthermore, EAAT3 is thought to be involved in facilitating GABA and glutathione biosynthesis. EAAT3 is a member of the EAAT family that mediates the uptake of glutamate into neuronal and glial cells of the mammalian CNS. Two transporters expressed primarily in glia, EAAT1 and EAAT2, are crucial for glutamate homeostasis in the adult mammalian brain and for rapid clearance of glutamate from the synaptic cleft. Three neuronal transporters (EAAT3, EAAT4, and EAAT5) appear to have additional functions in regulating and processing cellular excitability with EAAT3 being abundantly expressed throughout the CNS (EAAT4 is unique to Purkinje cells of the cerebellum and EAAT5 is expressed in rod photoreceptor and bipolar cells of the retina).

EAATs are assembled as trimers, and the existence of multiple isoforms raises the question of whether certain isoforms can form hetero-oligomers. In the mammalian brain, the specificity of excitatory synaptic transmission depends on rapid diffusion of glutamate away from active synapses and the powerful uptake capacity of glutamate transporters in astrocytes. The extent to which neuronal glutamate transporters influence the lifetime of glutamate in the extracellular space remains unclear, but it is thought to be minor. EAAT3, the predominant neuronal glutamate transporter at excitatory synapses in hippocampal area CA1, buffers glutamate released during synaptic events and prolongs the time course of its clearance by astrocytes. EAAT3 does not significantly alter activation of receptors in the synaptic cleft. Instead, it reduces recruitment of perisynaptic/extrasynaptic NR2B-containing NMDARs, thereby facilitating induction of long-term potentiation by short bursts of high-frequency stimulation. Specific EAAT3 inhibitors may have the potential to locally and specifically strengthen particular synapses.

Obsessive-compulsive disorder (OCD) is among the most common mental disorders (prevalence 1-3%), and is at least as prevalent as schizophrenia and bipolar disorder. In the United States, one in 50 adults suffers from OCD. OCD affects children and adolescents as well as adults. Roughly one third to one half of adults with OCD reports a childhood onset of the disorder, and the disorder is typically chronic in nature. Treatment consists of predominantly serotonergic TCAs (clomipramine) or SSRIs in combination with cognitive-behavioral therapy (CBT). Overall, response to these interventions is of some but still limited benefit (approximately comparable to antidepressant response in MDD), and given the chronicity of OCD, the unmet medical need remains very high. OCD has been linked to serotonin and glutamate abnormalities. The hypothesis of glutamate signaling dysfunction in OCD is based on findings from neuroimaging, animal models, positional cloning and treatment studies.

The obsessive-compulsive symptomatology in OCD has considerable phenomenological, epidemiological and possibly (aetio)-pathophysiological overlap with a core autism spectrum disorder criterion: "restricted, repetitive patterns of behavior, interests, or activities" (taken from proposed DSM-5 revision). In support of this notion, human genetics studies have linked both the serotonin transporter and EAAT3 (SLC1A1) genes to autism spectrum disorder (ASD) or rigid-compulsive behavior in ASD and to OCD.

In addition, obsessive-compulsive symptoms induced by antipsychotics in schizophrenic bipolar disorder patients have been linked to EAAT3 (SLC1A1) gene variants. Postmortem brain studies have shown that both classic and atypical antipsychotics reduce EAAT3, suggesting an involvement of this transporter in neuroleptic mechanisms beyond dopamine and serotonin modulation. Moreover, genetic variation in the human gene EAAT3 (SLC1A1) has been associated with antipsychotic drug response.

There is converging evidence from neurobiological data, human genetics, imaging studies and experimental treatments that EAAT3 is a key pathophysiological element in OCD and rigid-compulsive behavior in autism and in schizophrenia.

Curr. Opin. Pharmacol. 20, 116-123, 2015
J. Neurosci., 32, 2552-2563, 2012
J. Neurosci 29, 14581-14595, 2009
Arch. Gen. Psychiatry, 66, 408-416, 2009
Pharmacol. Ther. 107, 271-285, 2005
J. Neurochem. 98, 1007-1018, 2006
Nat. Neurosci., 9, 119-126, 2006

Compounds of formula I are distinguished by having valuable therapeutic properties. They can be used in the treatment or prevention of disorders, relating to EAAT3 inhibitors. The most preferred indications for compounds which are EAAT3 inhibitors are psychiatric disorders such as schizophrenia, bipolar disorder, obsessive-compulsive disorder or autism spectrum disorder.

The present invention relates to compounds of formula I and to their pharmaceutically acceptable salts, to their use in the treatment of psychiatric disorders such as schizophrenia, bipolar disorder, obsessive-compulsive disorder or autism spectrum disorder, to compounds of formulas I, IA, IB, IC, ID, IE, IF and IG as pharmaceutically active substances, to the processes for their production as well as to their use in the treatment or prevention of disorders, relating to EAAT3 inhibitors, such as schizophrenia, bipolar disorder, obsessive-compulsive disorder or autism spectrum disorder and to pharmaceutical compositions containing the compounds of formula IA A further object of the present invention is a method for the treatment or prophylaxis of psychiatric disorder such as schizophrenia, bipolar disorder, obsessive-compulsive disorder or autism spectrum disorder, which method comprises administering an effective amount of a compound of formula I to a mammal in need.

Furthermore, the invention includes all racemic mixtures, all their corresponding enantiomers and/or optical isomers, or analogues containing isotopes of hydrogen, fluorine, carbon, oxygen or nitrogen.

One object of the present invention are novel compounds of formula IA,

N-tert-Butyl-3-(4-fluorophenyl)-5-(1,2,4-triazol-4-yl)-benzamide
N-tert-Butyl-3-(4-fluorophenyl)-5-(3-methyl-1,2,4-triazol-4-yl)-benzamide
N-tert-Butyl-3-(4-chlorophenyl)-5-(3-methyl-1,2,4-triazol-4-yl)-benzamide
N-tert-Butyl-3-(3-methyl-1,2,4-triazol-4-yl)-5-[4-(trifluoromethyl)-phenyl]-benzamide
N-tert-Butyl-3-(3-tert-butyl-1,2,4-triazol-4-yl)-5-(4-fluorophenyl)-benzamide
N-tert-Butyl-3-(3-tert-butyl-1,2,4-triazol-4-yl)-5-(4-chlorophenyl)-benzamide
N-tert-Butyl-3-(3-tert-butyl-1,2,4-triazol-4-yl)-5-[4-(trifluoromethyl)-phenyl]-benzamide
N-tert-Butyl-3-(4-fluorophenyl)-5-(3-propan-2-yl-1,2,4-triazol-4-yl)-benzamide
N-tert-Butyl-3-(4-chlorophenyl)-5-(3-propan-2-yl-1,2,4-triazol-4-yl)-benzamide
N-tert-Butyl-3-(3-propan-2-yl-1,2,4-triazol-4-yl)-5-[4-(trifluoromethyl)-phenyl]-benzamide
N-tert-Butyl-3-(4-chlorophenyl)-5-[3-(hydroxymethyl)-1,2,4-triazol-4-yl]-benzamide
N-tert-Butyl-3-(4-chlorophenyl)-5-[3-(2-hydroxypropan-2-yl)-1,2,4-triazol-4-yl]-benzamide
N-tert-Butyl-3-(3,4-difluorophenyl)-5-(3-propan-2-yl-1,2,4-triazol-4-yl)-benzamide
N-tert-Butyl-3-(4-methoxyphenyl)-5-(3-propan-2-yl-1,2,4-triazol-4-yl)-benzamide
N-tert-Butyl-3-(4-chloro-3-fluorophenyl)-5-(3-propan-2-yl-1,2,4-triazol-4-yl)-benzamide
N-tert-Butyl-3-(4-fluoro-3-methyl-phenyl)-5-(3-propan-2-yl-1,2,4-triazol-4-yl)-benzamide
N-tert-Butyl-3-(3-fluoro-4-methyl-phenyl)-5-(3-propan-2-yl-1,2,4-triazol-4-yl)-benzamide
N-tert-Butyl-3-(4-methyl-phenyl)-5-(3-propan-2-yl-1,2,4-triazol-4-yl)-benzamide
N-tert-Butyl-3-(4-cyano-phenyl)-5-(3-propan-2-yl-1,2,4-triazol-4-yl)-benzamide or
N-tert-Butyl-3-(4-cyclopropyl-phenyl)-5-(3-propan-2-yl-1,2,4-triazol-4-yl)-benzamide.

One further object of the present invention are novel compounds of formula IB,

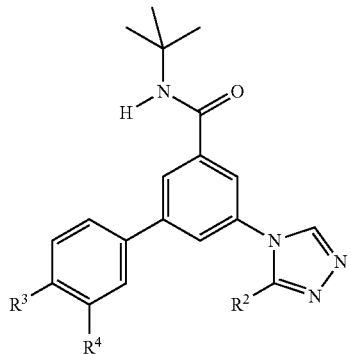

IA

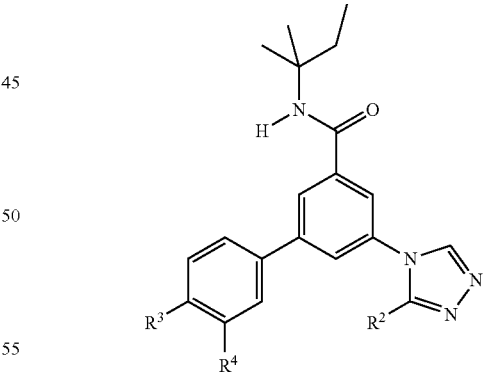

IB wherein
$R^2$ is hydrogen, methyl, ethyl, isopropyl, tert-butyl, cyclopropyl, hydroxmethyl, or 2-propyl-2-ol;
$R^3$ is Cl, F, CF$_3$, cyano, methyl, methoxy, isopropyl, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the following compounds:

wherein
$R^2$ is hydrogen, methyl, ethyl, isopropyl, tert-butyl, cyclopropyl, hydroxmethyl, or 2-propyl-2-ol;
$R^3$ is Cl, F, CF$_3$, cyano, methyl, methoxy, isopropyl, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the following compounds:

3-(4-Fluorophenyl)-N-(2-methylbutan-2-yl)-5-(1,2,4-triazol-4-yl)-benzamide
N-(2-Methylbutan-2-yl)-3-(3-propan-2-yl-1,2,4-triazol-4-yl)-5-[4-(trifluoromethyl)-phenyl]-benzamide
3-(4-Fluorophenyl)-N-(2-methylbutan-2-yl)-5-(3-propan-2-yl-1,2,4-triazol-4-yl)-benzamide or
3-(4-Chlorophenyl)-N-(2-methylbutan-2-yl)-5-(3-propan-2-yl-1,2,4-triazol-4-yl)-benzamide.

One object of the present invention are novel compounds of formula IC,

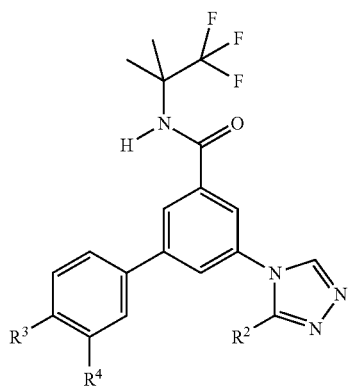

IC wherein
R² is hydrogen, methyl, ethyl, isopropyl, tert-butyl, cyclopropyl, hydroxmethyl, or 2-propyl-2-ol;
R³ is Cl, F, CF₃, cyano, methyl, methoxy, isopropyl, or cyclopropyl;
R⁴ is hydrogen, methyl, F or Cl;
or a pharmaceutically acceptable salt or acid addition salt, a racemic mixture, or its corresponding enantiomer and/or optical isomer and/or stereoisomer thereof, for example the following compound:
3-(4-Fluorophenyl)-5-(1,2,4-triazol-4-yl)-N-(1,1,1-trifluoro-2-methylpropan-2-yl)-benzamide.

One further object of the present invention are novel compounds of formula ID,

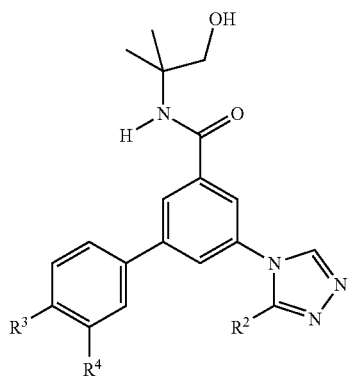

ID wherein
R² is hydrogen, methyl, ethyl, isopropyl, tert-butyl, cyclopropyl, hydroxmethyl, or 2-propyl-2-ol;
R³ is Cl, F, CF₃, cyano, methyl, methoxy, isopropyl, or cyclopropyl;
R⁴ is hydrogen, methyl, F or Cl;

or a pharmaceutically acceptable salt or acid addition salt, a racemic mixture, or its corresponding enantiomer and/or optical isomer and/or stereoisomer thereof, for example the following compounds:
3-(4-Fluorophenyl)-N-(1-hydroxy-2-methylpropan-2-yl)-5-(3-propan-2-yl-1,2,4-triazol-4-yl)-benzamide
3-(4-Chlorophenyl)-N-(1-hydroxy-2-methylpropan-2-yl)-5-(3-propan-2-yl-1,2,4-triazol-4-yl)-benzamide or
N-(1-hydroxy-2-methylpropan-2-yl)-3-(3-propan-2-yl-1,2,4-triazol-4-yl)-5-[4-(trifluoromethyl)-phenyl]-benzamide.

One object of the present invention are novel compounds of formula IE,

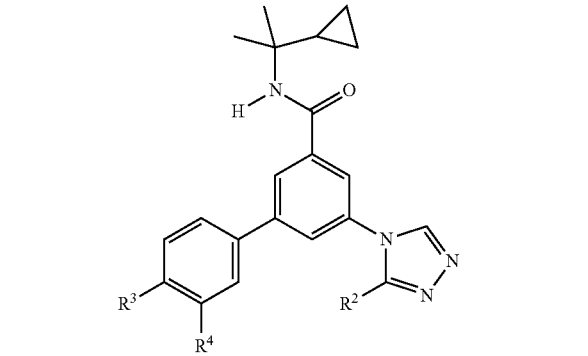

IE wherein
R² is hydrogen, methyl, ethyl, isopropyl, tert-butyl, cyclopropyl, hydroxmethyl, or 2-propyl-2-ol;
R³ is Cl, F, CF₃, cyano, methyl, methoxy, isopropyl, or cyclopropyl;
R⁴ is hydrogen, methyl, F or Cl;

or a pharmaceutically acceptable salt or acid addition salt, a racemic mixture, or its corresponding enantiomer and/or optical isomer and/or stereoisomer thereof, for example the following compounds:
N-(2-Cyclopropylpropan-2-yl)-3-(4-fluorophenyl)-5-(1,2,4-triazol-4-yl)-benzamide
3-(3-tert-Butyl-1,2,4-triazol-4-yl)-N-(2-cyclopropylpropan-2-yl)-5-[4-(trifluoromethyl)-phenyl]-benzamide
3-(3-tert-Butyl-1,2,4-triazol-4-yl)-N-(2-cyclopropylpropan-2-yl)-5-(4-fluorophenyl)-benzamide
3-(3-tert-Butyl-1,2,4-triazol-4-yl)-5-(4-chlorophenyl)-N-(2-cyclopropylpropan-2-yl)-benzamide
N-(2-Cyclopropylpropan-2-yl)-3-(4-fluorophenyl)-5-(3-propan-2-yl-1,2,4-triazol-4-yl)-benzamide
3-(4-Chlorophenyl)-N-(2-cyclopropyl-propan-2-yl)-5-(3-propan-2-yl-1,2,4-triazol-4-yl)-benzamide
N-(2-Cyclopropyl-propan-2-yl)-3-(3-propan-2-yl-1,2,4-triazol-4-yl)-5-[4-(trifluoromethyl)-phenyl]-benzamide or
3-(4-Chlorophenyl)-N-(2-cyclopropyl-propan-2-yl)-5-[3-(hydroxymethyl)-1,2,4-triazol-4-yl]-benzamide.

One further object of the invention are compounds of formula IF,

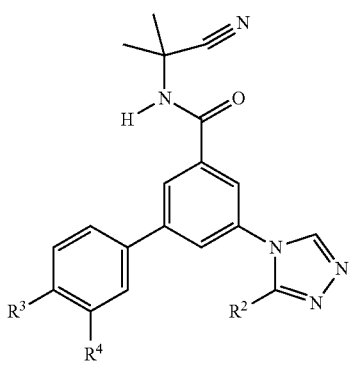

IF wherein
$R^2$ is hydrogen, methyl, ethyl, isopropyl, tert-butyl, cyclopropyl, hydroxmethyl, or 2-propyl-2-ol;
$R^3$ is Cl, F, $CF_3$, cyano, methyl, methoxy, isopropyl, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof.

One further object of the invention are compounds of formula IG,

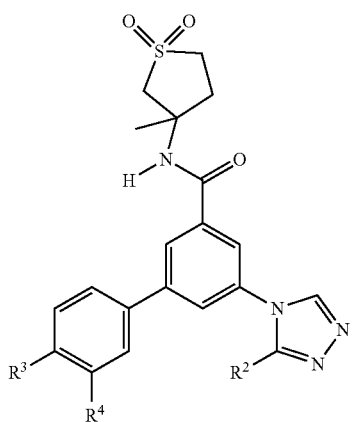

IG $R^2$ is hydrogen, methyl, ethyl, isopropyl, tert-butyl, cyclopropyl, hydroxmethyl, or 2-propyl-2-ol;
$R^3$ is Cl, F, $CF_3$, cyano, methyl, methoxy, isopropyl, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the following compound:
(RS)-3(4-Chlorophenyl)-5-[3-(hydroxymethyl)-1,2,4-triazol-4-yl]-N-(3-methyl-1,1-dioxothiolan-3-yl)-benzamide.

The preparation of compounds of formulas IA, IB, IC, ID, IE, IF and IG of the present invention may be carried out in sequential or convergent synthetic routes. Syntheses of the compounds of the invention are shown in the following schemes 1 to 6. The skills required for carrying out the reaction and purification of the resulting products are known to those skilled in the art. The substituents and indices used in the following description of the processes have the significance given herein before.

The compounds of formulas IA, IB, IC, ID, IE, IF and IG can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of IA, IB, IC, ID, IE, IF and IG and their pharmaceutically acceptable salts may be prepared by methods, known in the art, for example by the process variant described below, which process comprises
a) reacting a compound of formula II

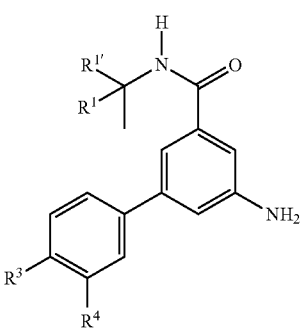

II with N,N-dimethylformamide-dimethylacetal

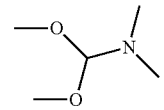

III and a compound of formula

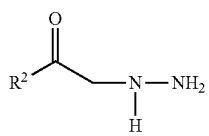

IV to a compound of formula I

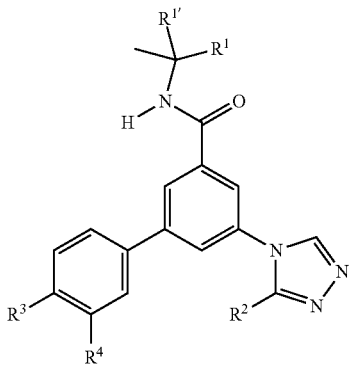

I b) reacting a compound of formula V

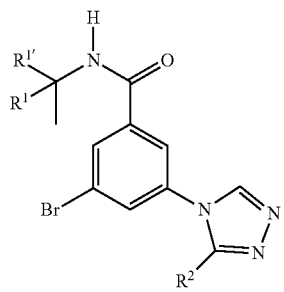

with a compound of formula III

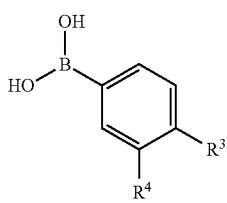

to a compound of formula I

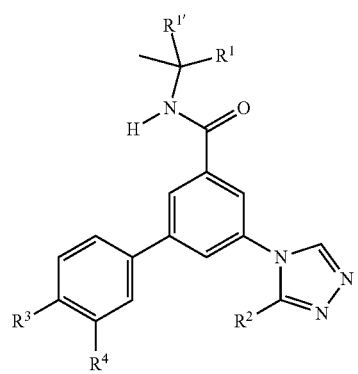

wherein the substituents are as described above, or
if desired, converting the compounds obtained into pharmaceutically acceptable acid addition salts, or
c) reacting a compound of formula VII

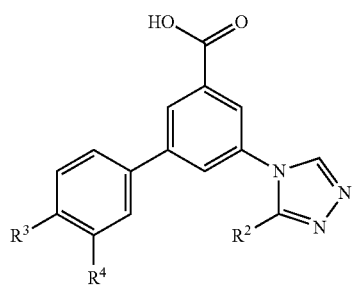

with a compound of formula VIII

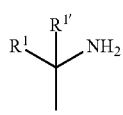

to a compound of formula I

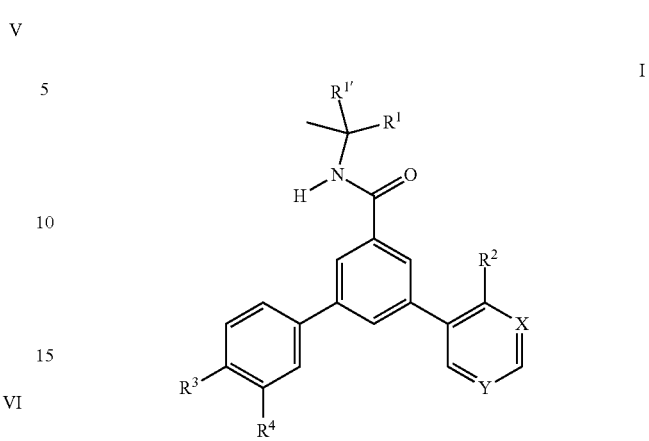

wherein the substituents are described above, or
if desired, converting the compounds obtained into pharmaceutically acceptable acid addition salts.

The preparation of compounds of formulas IA, IB, IC, ID, IE, IF and IG is further described in more detail in schemes below and in examples 1-37.

In general the triazole derivatives I can either be prepared from the intermediate aniline derivatives II by well-known trizole formation with N,N-dimthylformamide-dimethylacetal III and commercially available acyl-hydrazides IV,

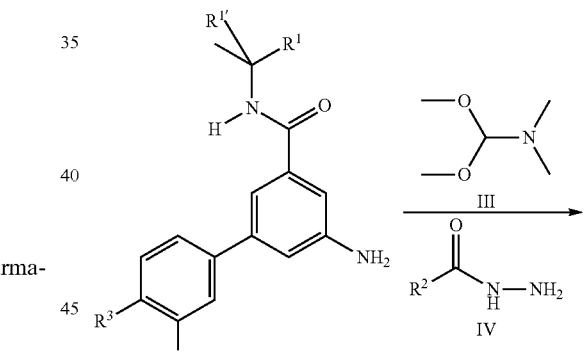

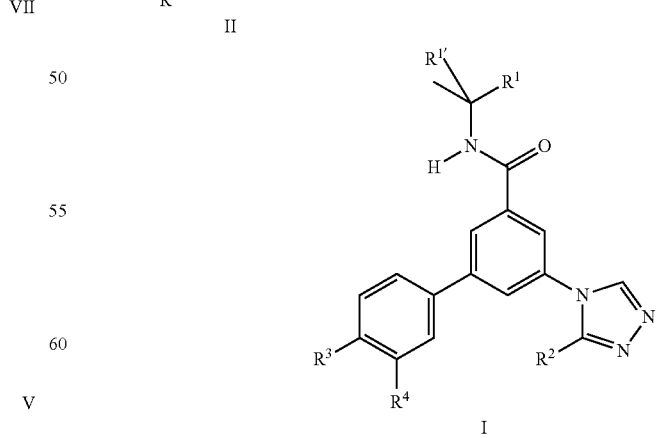

or by coupling reaction of the bromo derivatives V with commercially available boronic acid derivatives VI,

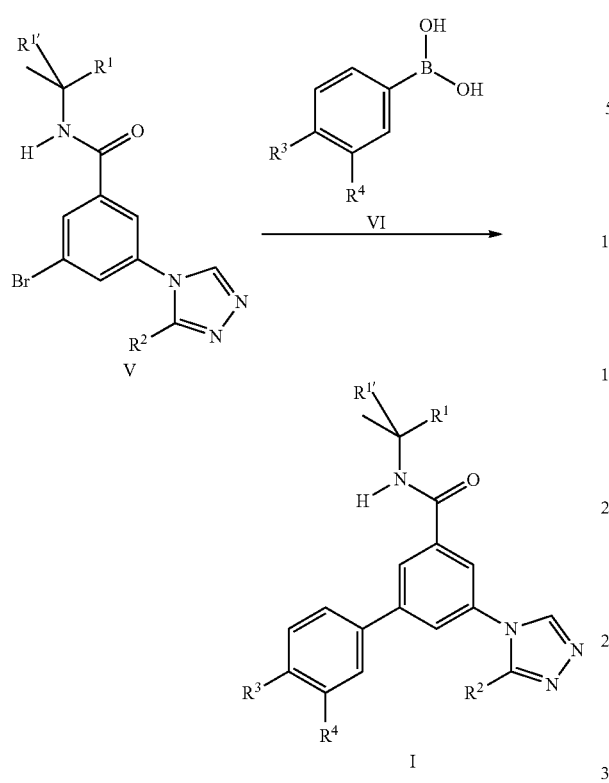

or by amide formation using the acid derivatives VII and the commercially available amines VIII.

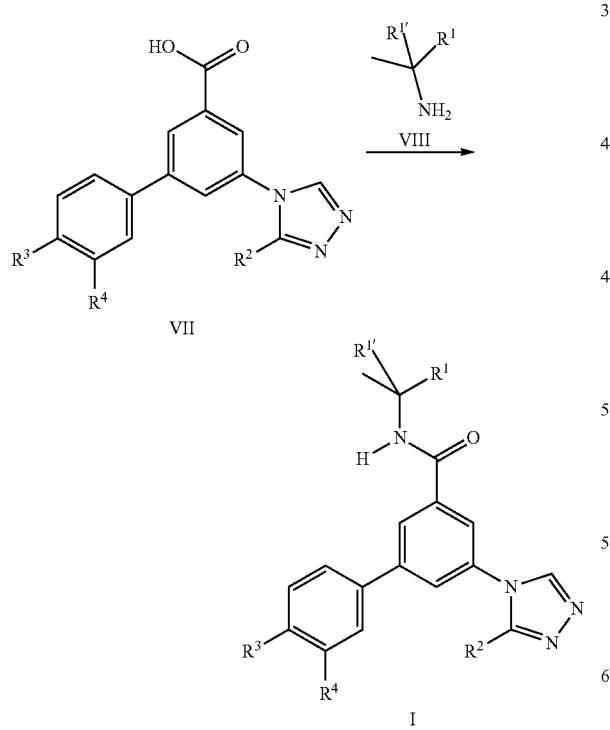

The aniline derivatives II can be prepared starting from commercially available 3-iodo-5-nitrobenzoic acid IX. Amide formation with the commercially available amines VIII using standard conditions leads to the amides X which can coupled with commercially available boronic acid derivatives VI to yield the nitro compounds XI which can be reduced with tin(II)chloride to yield the aniline building blocks II.

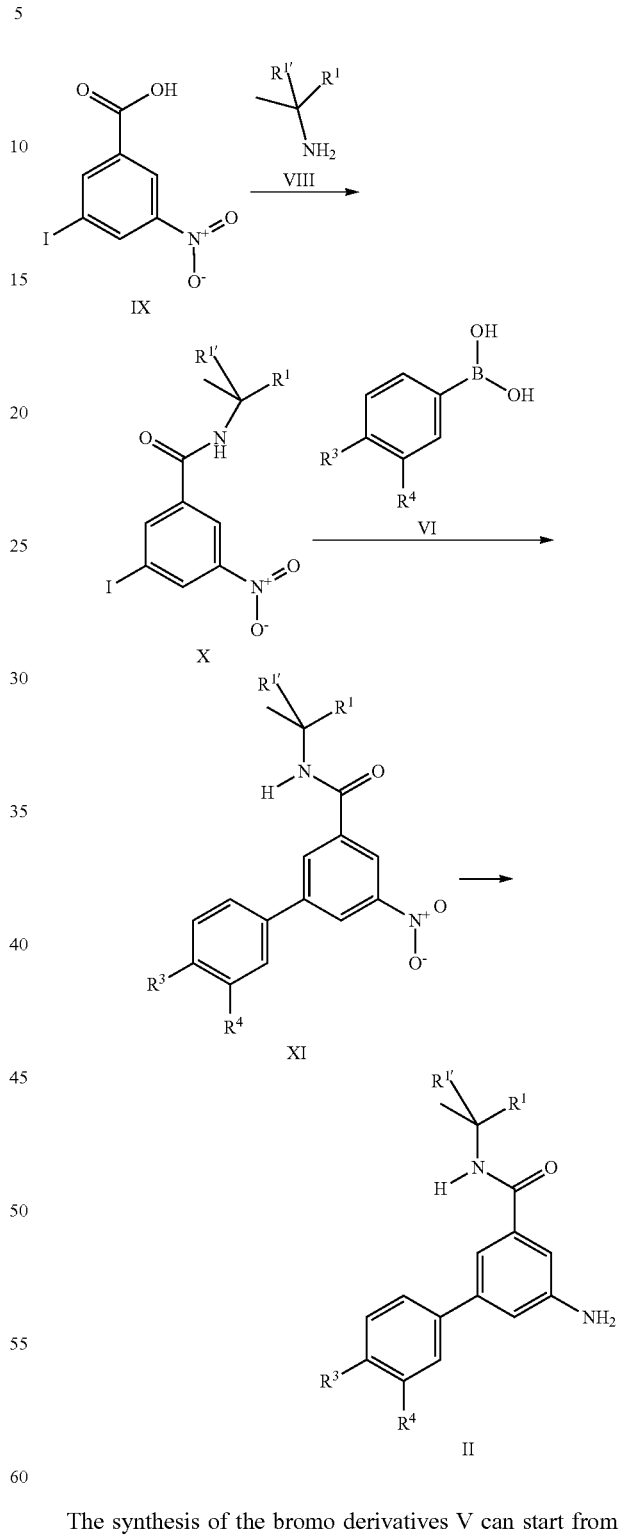

The synthesis of the bromo derivatives V can start from the commercially available 3-amino-5-bromobenzoic acid XII. Triazole formation by reaction with the N-[(E)-dimethylamino-methylidene-amino]-acylamides XIII prepared from commercially available acyl-hydrazides IV and N,N-dimthylformamide-dimethylacetal III yields the triazole derivatives XIV. Amide formation with the commercially available amines VIII led to the building blocks V.

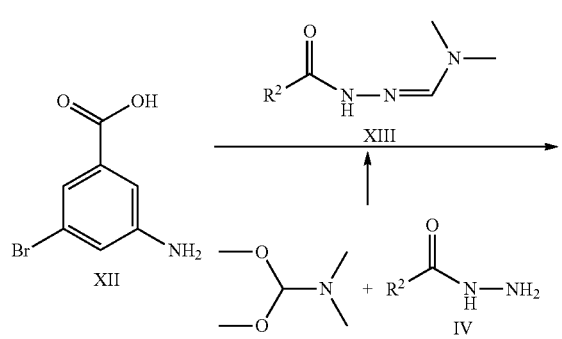

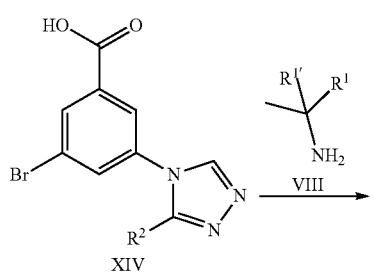

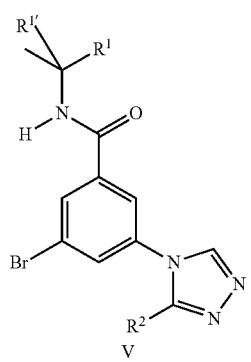

An alternative route for the synthesis of the triazole derivatives I can start from the commercially available 3-amino-5-bromobenzoic acid XII. Triazole formation using N,N-dimthylformamide-dimethylacetal III and commercially available acyl-hydrazides IV, yields the ester derivatives XV. Coupling reaction with commercially available boronic acid derivatives VI and subsequent ester hydrolysis led to the acid building blocks VII.

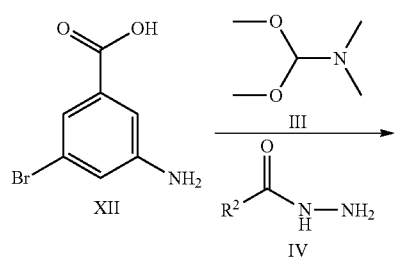

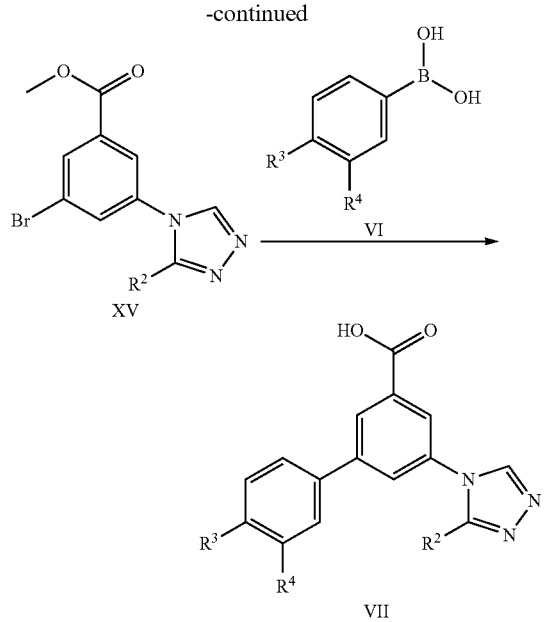

An alternative route to the tetrazole building block XIV-1 ($R^2$=H) is the condensation of the commercially available 3-amino-5-bromobenzoic acid XII with commercially available 1,2-diformylhydrazine XVI.

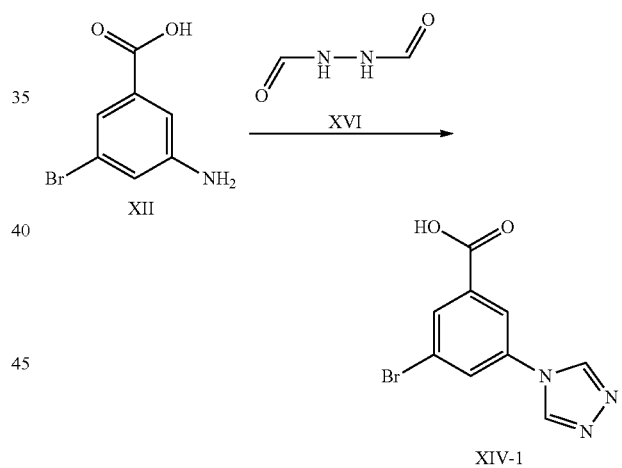

Generally speaking, the sequence of steps used to synthesize the compounds of formula I can also be modified in certain cases.

The compounds of formula I and their pharmaceutically usable addition salts possess valuable pharmaceutical properties. Specifically, it has been found that the compounds of the present invention are EAAT3 inhibitors for use in the treatment of schizophrenia, bipolar disorder, obsessive-compulsive disorder or autism spectrum disorders.

The compounds were investigated in accordance with the test given hereinafter.

Biological Assay and Data

The FLIPR Membrane Potential (FMP) Assay

HEK-293 cells stably expressing human EAAT3 were seeded at 55 000 cells/well in growth medium (DMEM glutamate free (Invitrogen 11960-044), 1% Pen Strep (10 ml/l GIBCO BRL N°15140-023), 10% FCS non dialysed heat inactivated, 5 mg/l puromycin) in poly-D-lysine treated 96-well black microtiter plates with clear-bottom. After 24 h, the growth medium was removed and 100 μl/well of Krebs buffer (140 mM NaCl, 4.7 mM KCl, 2.5 mM $CaCl_2$, 1.2 mM $MgCl_2$, 11 mM HEPES, 10 mM D-glucose, pH=7.4) added. The cells were then loaded by adding 100 μl/well FMP assay dye (FLIPR Membrane Potential assay reagent, Molecular Devices). The 96-well plates were then incubated at 37° C. for 1 h. The depolarization of the cells will cause more dye to enter in the cells, where it will bind to intracellular proteins and lipids and cause an increase in the fluorescence signal. Antagonist potency at human EAAT3 was determined by using L-glutamate as agonist at a concentration which gives 80% of the maximum response. The antagonists were applied 15 min before the application of the agonist L-glutamate. The assays were performed at room temperature and measurements done by using a Fluorometric Imaging Plate Reader (FLIPR, Molecular Devices) and filter #2. Responses were measured as peak increase in fluorescence minus basal (i.e. fluorescence without addition of L-glutamate). Kb was determined using the Cheng-Prusoff equation $Kb=IC_{50}/[1+(A/EC_{50})]$, where $IC_{50}$ is the concentration of the antagonist producing 50% inhibition, A is the concentration of the agonist against which the $IC_{50}$ is being determined (at $EC_{80}$) and $EC_{50}$ is the concentration of the agonist producing 50% inhibition.

List of Examples and Data:

| | Structure | Compound name | EAAT3 Kb [uM] |
|---|---|---|---|
| 1 | 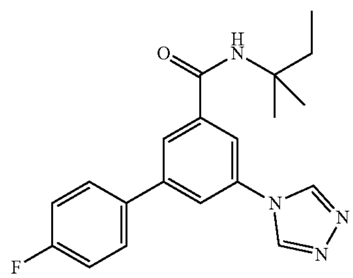 [SMILES: CCC(C)(C)NC(=O)c1cc(-c2ccc(F)cc2)cc(-n2cnnc2)c1] | 3-(4-Fluorophenyl)-N-(2-methylbutan-2-yl)-5-(1,2,4-triazol-4-yl)-benzamide | 0.088 |
| 2 | 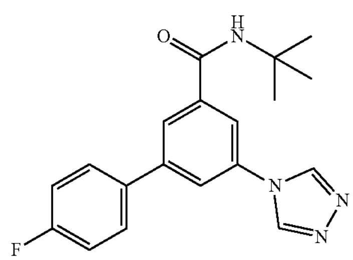 [SMILES: CC(C)(C)NC(=O)c1cc(-c2ccc(F)cc2)cc(-n2cnnc2)c1] | N-tert-Butyl-3-(4-fluorophenyl)-5-(1,2,4-triazol-4-yl)-benzamide | 0.29 |
| 3 | 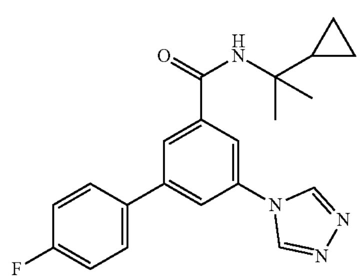 [SMILES: CC(C)(NC(=O)c1cc(-c2ccc(F)cc2)cc(-n2cnnc2)c1)C1CC1] | N-(2-Cyclopropylpropan-2-yl)-3-(4-fluorophenyl)-5-(1,2,4-triazol-4-yl)-benzamide | 0.39 |
| 4 | 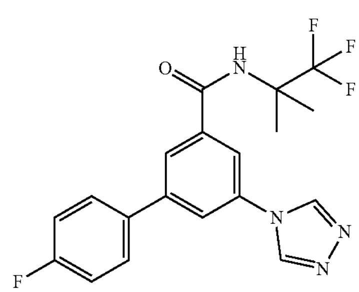 [SMILES: CC(C)(NC(=O)c1cc(-c2ccc(F)cc2)cc(-n2cnnc2)c1)C(F)(F)F] | 3-(4-Fluorophenyl)-5-(1,2,4-triazol-4-yl)-N-(1,1,1-trifluoro-2-methylpropan-2-yl)-benzamide | 0.25 |

-continued
| | Structure | Compound name | EAAT3 Kb [uM] |
|---|---|---|---|
| 5 | 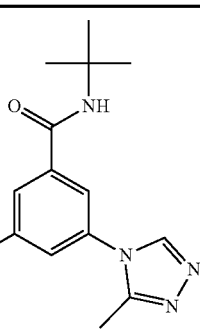 | N-tert-Butyl-3-(4-fluorophenyl)-5-(3-methyl-1,2,4-triazol-4-yl)-benzamide | 0.16 |
| 6 | 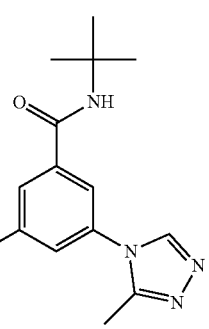 | N-tert-Butyl-3-(4-chlorophenyl)-5-(3-methyl-1,2,4-triazol-4-yl)-benzamide | 0.076 |
| 7 | 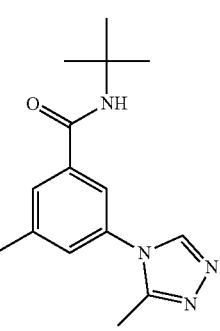 | N-tert-Butyl-3-(3-methyl-1,2,4-triazol-4-yl)-5[4-(trifluoromethyl)-phenyl]-benzamide | 0.13 |
| 8 | 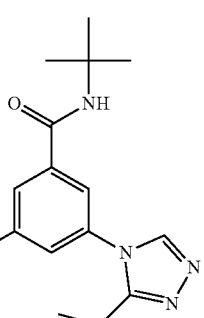 | N-tert-Butyl-3-(3-tert-butyl-1,2,4-triazol-4-yl)-5-(4-fluorophenyl)-benzamide | 0.19 |

| | Structure | Compound name | EAAT3 Kb [uM] |
|---|---|---|---|
| 9 | 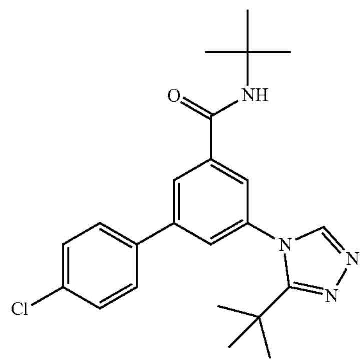 [SMILES: CC(C)(C)NC(=O)c1cc(-c2ccc(Cl)cc2)cc(-n2cnnc2C(C)(C)C)c1] | N-tert-Butyl-3-(3-tert-butyl-1,2,4-triazol-4-yl)-5-(4-chlorophenyl)-benzamide | 0.18 |
| 10 | 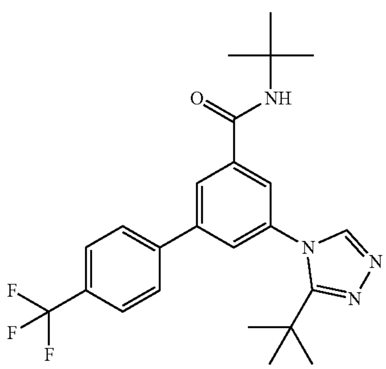 [SMILES: CC(C)(C)NC(=O)c1cc(-c2ccc(C(F)(F)F)cc2)cc(-n2cnnc2C(C)(C)C)c1] | N-tert-Butyl-3-(3-tert-butyl-1,2,4-triazol-4-yl)-5-[4-(trifluoromethyl)-phenyl]-benzamide | 0.16 |
| 11 | 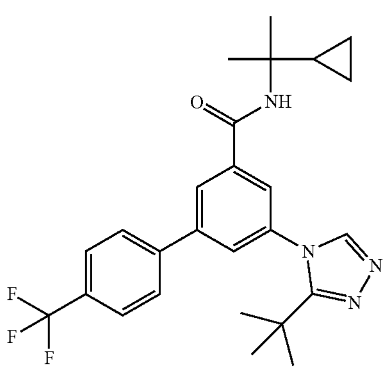 [SMILES: CC(C)(C)c1nncn1-c1cc(C(=O)NC(C)(C)C2CC2)cc(-c2ccc(C(F)(F)F)cc2)c1] | 3-(3-tert-Butyl-1,2,4-triazol-4-yl)-N-(2-cyclopropylpropan-2-yl)-5[4-(trifluoromethyl)-phenyl]-benzamide | 0.18 |
| 12 | 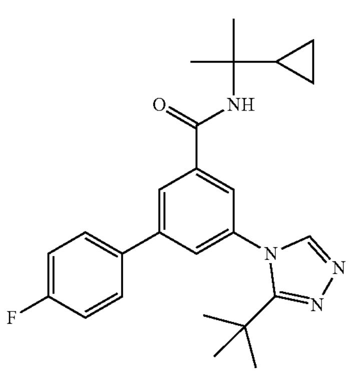 [SMILES: CC(C)(C)c1nncn1-c1cc(C(=O)NC(C)(C)C2CC2)cc(-c2ccc(F)cc2)c1] | 3-(3-tert-Butyl-1,2,4-triazol-4-yl)-N-(2-cyclopropylpropan-2-yl)-5-(4-fluorophenyl)-benzamide | 0.15 |

-continued

| | Structure | Compound name | EAAT3 Kb [uM] |
|---|---|---|---|
| 13 | 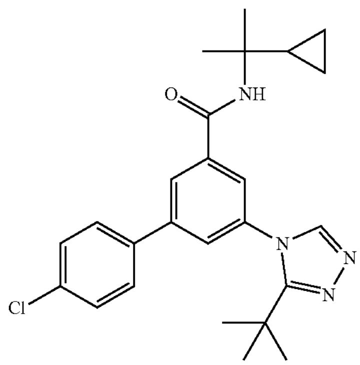 [SMILES: CC(C)(C)c1nncn1-c1cc(C(=O)NC(C)(C)C2CC2)cc(-c2ccc(Cl)cc2)c1] | 3-(3-tert-Butyl-1,2,4-triazol-4-yl)-5-(4-chlorophenyl)-N-(2-cyclopropylpropan-2-yl)-benzamide | 0.29 |
| 14 | 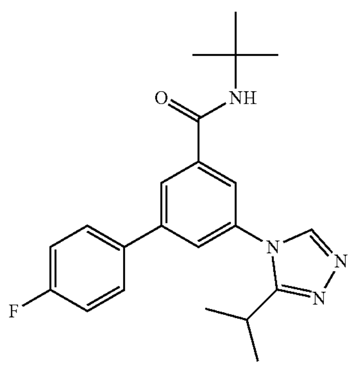 [SMILES: CC(C)c1nncn1-c1cc(C(=O)NC(C)(C)C)cc(-c2ccc(F)cc2)c1] | N-tert-Butyl-3-(4-fluorophenyl)-5-(3-propan-2-yl-1,2,4-triazol-4-yl)-benzamide | 0.075 |
| 15 | 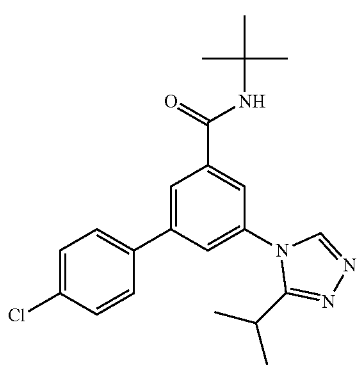 [SMILES: CC(C)c1nncn1-c1cc(C(=O)NC(C)(C)C)cc(-c2ccc(Cl)cc2)c1] | N-tert-Butyl-3-(4-chlorophenyl)-5-(3-propan-2-yl-1,2,4-triazol-4-yl)-benzamide | 0.075 |
| 16 | 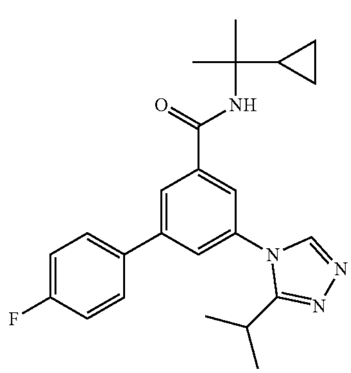 [SMILES: CC(C)c1nncn1-c1cc(C(=O)NC(C)(C)C2CC2)cc(-c2ccc(F)cc2)c1] | N-(2-Cyclopropylpropan-2-yl)-3-(4-fluorophenyl)-5-(3-propan-2-yl-1,2,4-triazol-4-yl)-benzamide | 0.1 |

-continued

| | Structure | Compound name | EAAT3 Kb [uM] |
|---|---|---|---|
| 17 | 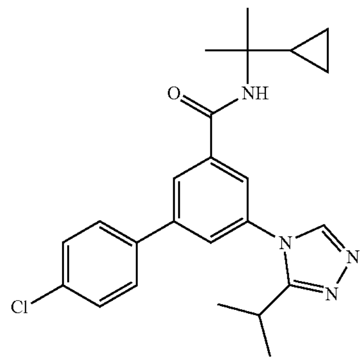 [SMILES: CC(C)c1nncn1-c1cc(C(=O)NC(C)(C)C2CC2)cc(-c2ccc(Cl)cc2)c1] | 3-(4-Chlorophenyl)-N-(2-cyclopropyl-propan-2-yl)-5-(3-propan-2-yl-1,2,4-triazol-4-yl)-benzamide | 0.19 |
| 18 | 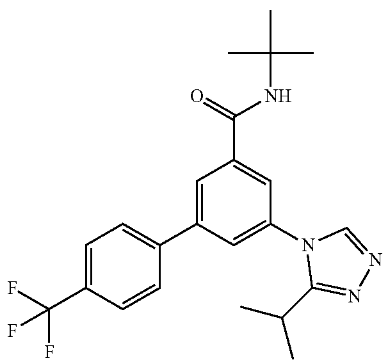 [SMILES: CC(C)c1nncn1-c1cc(C(=O)NC(C)(C)C)cc(-c2ccc(C(F)(F)F)cc2)c1] | N-tert-Butyl-3-(3-propan-2-yl-1,2,4-triazol-4-yl)-5-[4-(trifluoromethyl)-phenyl]-benzamide | 0.13 |
| 19 | 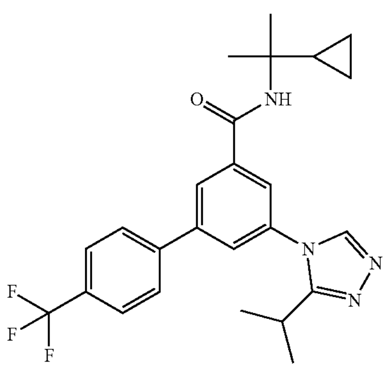 [SMILES: CC(C)c1nncn1-c1cc(C(=O)NC(C)(C)C2CC2)cc(-c2ccc(C(F)(F)F)cc2)c1] | N-(2-Cyclopropyl-propan-2-yl)-3-(3-propan-2-yl-1,2,4-triazol-4-yl)-5-[4-(trifluoromethyl)-phenyl]-benzamide | 0.22 |
| 20 | 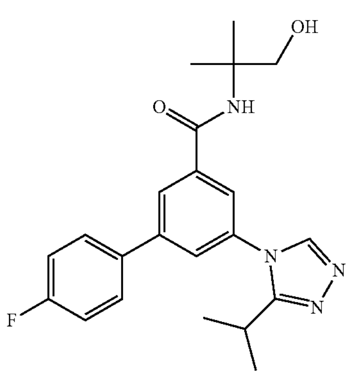 [SMILES: CC(C)c1nncn1-c1cc(C(=O)NC(C)(C)CO)cc(-c2ccc(F)cc2)c1] | 3-(4-Fluorophenyl)-N-(1-hydroxy-2-methylpropan-2-yl)-5-(3-propan-2-yl-1,2,4-triazol-4-yl)-benzamide | 0.39 |

-continued
| | Structure | Compound name | EAAT3 Kb [uM] |
|---|---|---|---|
| 21 | 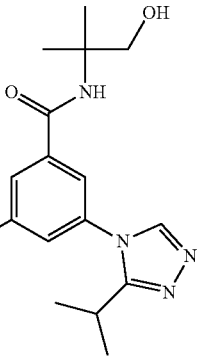 | 3-(4-Chlorophenyl)-N-(1-hydroxy-2-methylpropan-2-yl)-5-(3-propan-2-yl-1,2,4-triazol-4-yl)-benzamide | 0.23 |
| 22 | 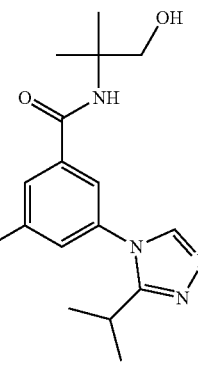 | N-(1-hydroxy-2-methylpropan-2-yl)-3-(3-propan-2-yl-1,2,4-triazol-4-yl)-5-[4-(trifluoromethyl)-phenyl]-benzamide | 0.33 |
| 23 | 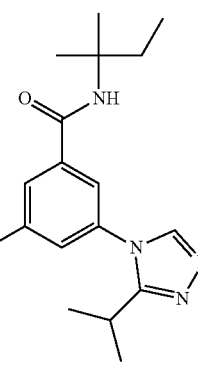 | N-(2-Methylbutan-2-yl)-3-(3-propan-2-yl-1,2,4-triazol-4-yl)-5-[4-(trifluoromethyl)-phenyl]-benzamide | 0.094 |
| 24 | 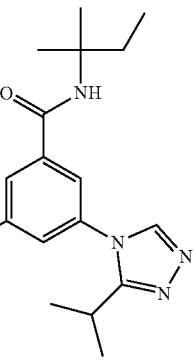 | 3-(4-Fluorophenyl)-N-(2-methylbutan-2-yl)-5-(3-propan-2-yl-1,2,4-triazol-4-yl)-benzamide | 0.054 |

| | Structure | Compound name | EAAT3 Kb [uM] |
|---|---|---|---|
| 25 | 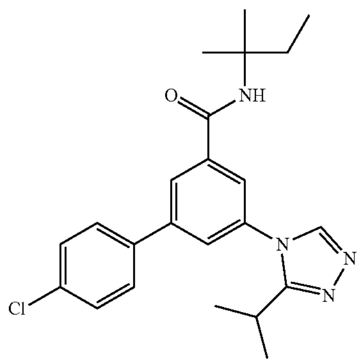 [SMILES: CCC(C)(C)NC(=O)c1cc(-c2ccc(Cl)cc2)cc(-n2cnnc2C(C)C)c1] | 3-(4-Chlorophenyl)-N-(2-methylbutan-2-yl)-5-(3-propan-2-yl-1,2,4-triazol-4-yl)-benzamide | 0.12 |
| 26 | 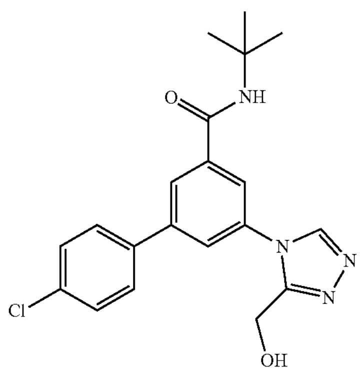 [SMILES: CC(C)(C)NC(=O)c1cc(-c2ccc(Cl)cc2)cc(-n2cnnc2CO)c1] | N-tert-Butyl-3-(4-chlorophenyl)-5-[3-(hydroxymethyl)-1,2,4-triazol-4-yl]-benzamide | 0.145 |
| 27 | 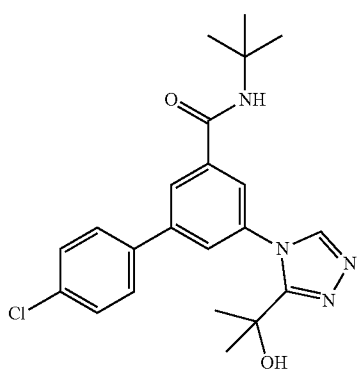 [SMILES: CC(C)(C)NC(=O)c1cc(-c2ccc(Cl)cc2)cc(-n2cnnc2C(C)(C)O)c1] | N-tert-Butyl-3-(4-chlorophenyl)-5-[3-(2-hydroxypropan-2-yl)-1,2,4-triazol-4-yl]-benzamide | 0.064 |
| 28 | 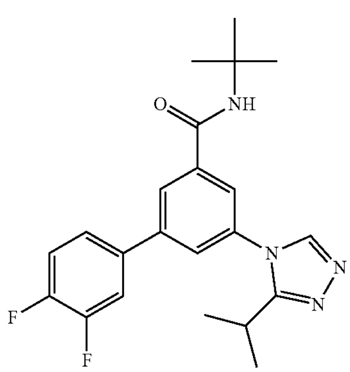 [SMILES: CC(C)c1nncn1-c1cc(C(=O)NC(C)(C)C)cc(-c2ccc(F)c(F)c2)c1] | N-tert-Butyl-3-(3,4-difluorophenyl)-5-(3-propan-2-yl-1,2,4-triazol-4-yl)-benzamide | 0.16 |

-continued
| | Structure | Compound name | EAAT3 Kb [uM] |
|---|---|---|---|
| 29 | 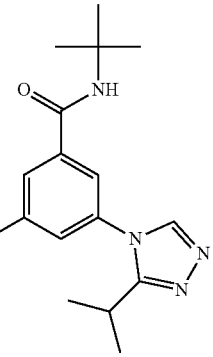 | N-tert-Butyl-3-(4-methoxyphenyl)-5-(3-propan-2-yl-1,2,4-triazol-4-yl)-benzamide | 0.29 |
| 30 | 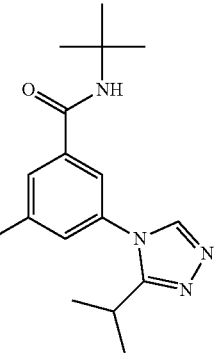 | N-tert-Butyl-3-(4-chloro-3-fluorophenyl)-5-(3-propan-2-yl-1,2,4-triazol-4-yl)-benzamide | 0.1 |
| 31 | 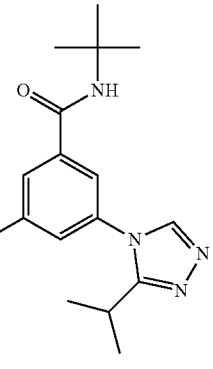 | N-tert-Butyl-3-(4-fluoro-3-methyl-phenyl)-5-(3-propan-2-yl-1,2,4-triazol-4-yl)-benzamide | 0.098 |
| 32 | 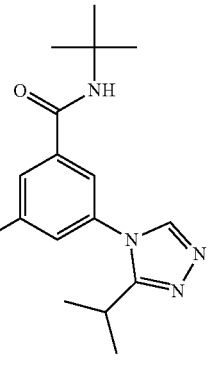 | N-tert-Butyl-3-(3-fluoro-4-methyl-phenyl)-5-(3-propan-2-yl-1,2,4-triazol-4-yl)-benzamide | 0.12 |

-continued
| | Structure | Compound name | EAAT3 Kb [uM] |
|---|---|---|---|
| 33 | 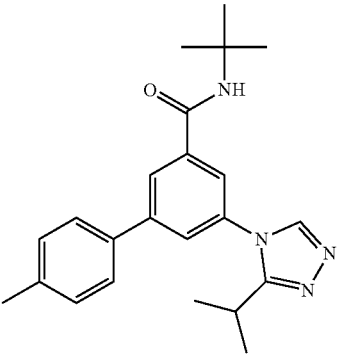 [SMILES: Cc1ccc(-c2cc(C(=O)NC(C)(C)C)cc(-n3cnnc3C(C)C)c2)cc1] | N-tert-Butyl-3-(4-methyl-phenyl)-5-(3-propan-2-yl-1,2,4-triazol-4-yl)-benzamide | 0.1 |
| 34 | 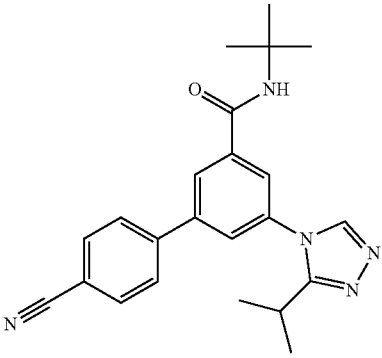 [SMILES: CC(C)c1nncn1-c1cc(C(=O)NC(C)(C)C)cc(-c2ccc(C#N)cc2)c1] | N-tert-Butyl-3-(4-cyano-phenyl)-5-(3-propan-2-yl-1,2,4-triazol-4-yl)-benzamide | 0.22 |
| 35 | 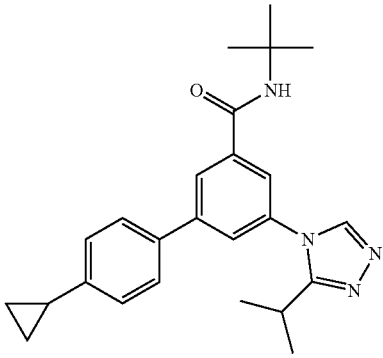 [SMILES: CC(C)c1nncn1-c1cc(C(=O)NC(C)(C)C)cc(-c2ccc(C3CC3)cc2)c1] | N-tert-Butyl-3-(4-cyclopropyl-phenyl)-5-(3-propan-2-yl-1,2,4-triazol-4-yl)-benzamide | 0.13 |
| 36 | 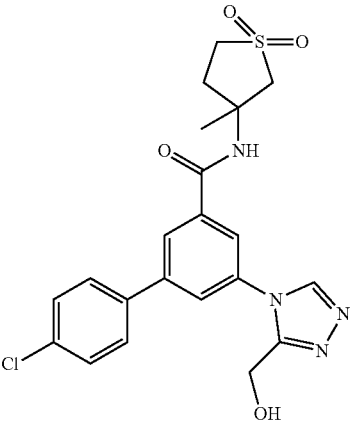 [SMILES: CC1(NC(=O)c2cc(-c3ccc(Cl)cc3)cc(-n3cnnc3CO)c2)CCS(=O)(=O)C1] | (RS)-3-(4-Chlorophenyl)-5-[3-(hydroxymethyl)-1,2,4-triazol-4-yl]-N-(3-methyl-1,1-dioxothiolan-3-yl)-benzamide | 1.57 |

| Structure | Compound name | EAAT3 Kb [uM] |
|---|---|---|
| 37 | 3-(4-Chlorophenyl)-N-(2-cyclopropyl-propan-2-yl)-5-[3-(hydroxymethyl)-1,2,4-triazol-4-yl]-benzamide | 0.15 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions comprising Compounds of the Invention Tablets of the following composition are manufactured in the usual manner:

| | mg/tablet | | | |
|---|---|---|---|---|
| ingredient | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXPERIMENTAL SECTION

Intermediates

Intermediate 1: 3-(4-Fluorophenyl)-5-(1,2,4-triazol-4-yl)-benzoic acid

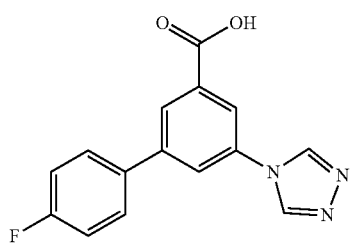 [SMILES: O=C(O)c1cc(-c2ccc(F)cc2)cc(-n2cnnc2)c1]

Step A

To a stirred mixture of commercially available 3-amino-5-bromobenzoic acid (0.50 g, 2.31 mmol), commercially available 1,2-diformylhydrazine (611 mg, 6.94 mmol) and pyridine (2.5 ml) was added dropwise at room temperature chlorotrimethylsilane (5.03 g, 5.87 ml, 46.3 mmol) and triethylamine (1.64 g, 2.26 ml, 16.2 mmol). The mixture was alloed to stir for 5 h at 100° C., cooled to room temperature, diluted with water (50 ml) and the precipitate collected by filtration to yield 3-bromo-5-(1,2,4-triazol-4-yl)-benzoic acid (0.61 g, 98%) as a light brown solid, MS (ISP) m/z=268.0 [(M+H)$^+$], mp 281.5° C.

Step B

A mixture of 3-bromo-5-(1,2,4-triazol-4-yl)-benzoic acid (0.30 g, 1.13 mmol) and (4-fluorophenyl)boronic acid (206 mg, 1.47 mmol), 1,2-dimethoxyethane (7.55 ml) and 2M sodium carbonate solution (1.89 ml, 3.78 mmol) was purged with argon in an ultrasonic bath for 5 min, triphenylphosphine (59.5 mg, 227 μmol) and palladium(II)acetate (25.5 mg, 113 μmol) were added and the reaction mixture was allowed to stir for 5 h under reflux conditions. The reaction mixture was cooled to room temperature, 2N NaOH (2 ml) was added, and the reaction mixture was allowed to stir for 30 min at room temperature. The organic phase was separated, the inorganic layer was adjusted to pH=2 with concentrated HCl solution, and the resulting precipitate was collected by filtration to yield the tile compound (0.24 g, 75%) as a light brown solid, MS (ISP) m/z=284.1 [(M+H)$^+$], mp 329° C.

Intermediate 2: 3-Bromo-N-tert-butyl-5-(3-methyl-1,2,4-triazol-4-yl)-benzamide

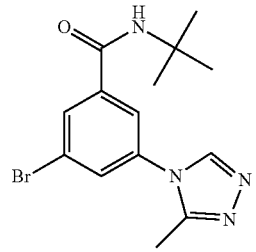 [SMILES: Cc1nncn1-c1cc(Br)cc(C(=O)NC(C)(C)C)c1]

Step A

A solution of commercially available acetohydrazide (1 g, 13.5 mmol) and commercially available 1,1-dimethoxy-N,N-dimethylmethan-amine (1.61 g, 1.79 ml, 13.5 mmol) in dichloromethane (9 ml) was allowed to stir for 30 min under reflux conditions, and was evaporated to yield N-[(E)-dimethylamino-methylidene-amino]-acetamide (1.72 g, 99%) as a light yellow solid, MS (ISP) m/z=130.1 [(M+H)$^+$].

Step B

In a sealed tube a mixture of commercially available 3-amino-5-bromobenzoic acid (1.99 g, 9.21 mmol), N-[(E)-dimethylamino-methylidene-amino]-acetamide (1.27 g, 9.85 mmol) and acetic acid (5 ml) was irradiated in a microwave oven for 15 min at 160° C. To the solution was added water (10 ml), the mixture was allowed to stir for 30 min at room temperature and the precipitate was collected by filtration. Reverse phase chromatography (acetonitrile/formic acid 48:52) yielded 3-bromo-5-(3-methyl-1,2,4-triazol-4-yl)-benzoic acid (0.24 g, 75%) as an off-white solid, MS (ISP) m/z=284.0 [(M+H)$^+$], mp 290.5° C.

Step C

To a stirred solution of 3-bromo-5-(3-methyl-1,2,4-triazol-4-yl)-benzoic acid (0.5 g, 1.77 mmol) in THF (13 ml) was added N,N-diisopropylethylamine (573 mg, 774 4.43 mmol), 2-methylpropan-2-amine (159 mg, 228 2.13 mmol) and TBTU (911 mg, 2.84 mmol). The reaction mixture was allowed to stir at room temperature for 17 h, evaporated and purified by flash chromatography [heptane/ethyl acetate (20-100%)] to yield the title compound (0.30 g, 50%) as a white solid, MS (ISP) m/z=337.1 [(M+H)+], mp 224.5° C.

Intermediate 3: 3-Bromo-N-tert-butyl-5-(3-tert-butyl-1,2,4-triazol-4-yl)-benzamide

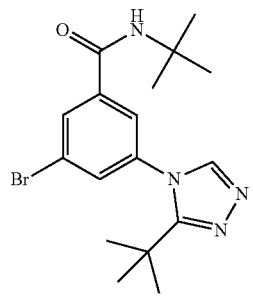 [SMILES: CC(C)(C)NC(=O)c1cc(Br)cc(-n2cnnc2C(C)(C)C)c1]

Step A

N-[(E)-Dimethylamino-methylideneamino]-2,2-dimethylpropanamide, white solid (2.12 g, 92%), MS (ISP) m/z=172.1 [(M+H)+], mp 131° C., was prepared in accordance with the general method of intermediate 2, step A, from commercially available pivalohydrazide (1.57 g, 13.5 mmol) and commercially available 1,1-dimethoxy-N,N-dimethylmethan-amine (1.61 g, 1.79 ml, 13.5 mmol).

Step B

3-Bromo-5-(3-tert-butyl-1,2,4-triazol-4-yl)-benzoic acid, white solid (0.63 g, 17%), MS (ISP) m/z=324.0 [(M+H)+], mp 302.5° C., was prepared in accordance with the general method of intermediate 2, step B, from commercially available 3-amino-5-bromobenzoic acid (2.48 g, 11.5 mmol) and N-[(E)-dimethylamino-methylideneamino]-2,2-dimethylpropanamide (2.10 g, 12.3 mmol).

Step C

The title compound, white solid (0.36 g, 98%), MS (ISP) m/z=381.1 [(M+H)+], mp 189° C., was prepared in accordance with the general method of intermediate 2, step C, from 3-bromo-5-(3-tert-butyl-1,2,4-triazol-4-yl)-benzoic acid (314 mg, 0.97 mmol) and 2-methyl-propan-2-amine (84.8 mg, 1.16 mmol).

Intermediate 4: 3-Bromo-5-(3-tert-butyl-1,2,4-triazol-4-yl)-N-(2-cyclopropylpropan-2-yl)-benzamide

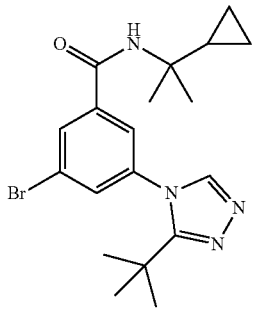 [SMILES: CC(C)(C)c1nncn1-c1cc(Br)cc(C(=O)NC(C)(C)C2CC2)c1]

The title compound, light yellow foam (0.39 g, 99%), MS (ISP) m/z=407.2 [(M+H)+], mp 60.5° C., was prepared in accordance with the general method of intermediate 2, step C, from 3-bromo-5-(3-tert-butyl-1,2,4-triazol-4-yl)-benzoic acid (intermediate 3, step B) (314 mg, 0.97 mmol) and 2-cyclopropylpropan-2-amine hydrochloride (158 mg, 1.16 mmol).

Intermediate 5: 3-Bromo-N-tert-butyl-5-(3-propan-2-yl-1,2,4-triazol-4-yl)-benzamide

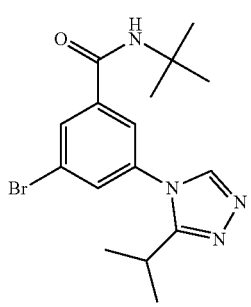 [SMILES: CC(C)c1nncn1-c1cc(Br)cc(C(=O)NC(C)(C)C)c1]

Step A

N-[(E)-Dimethylamino-methylideneamino]-2-methylpropanamide, white solid (2.11 g, 99%), MS (ISP) m/z=158.1 [(M+H)+], mp 131° C., was prepared in accordance with the general method of intermediate 2, step A, from commercially available isobutyrohydrazide (1.38 g, 13.5 mmol) and commercially available 1,1-dimethoxy-N,N-dimethylmethan-amine (1.61 g, 1.79 ml, 13.5 mmol).

Step B

3-Bromo-5-(3-propan-2-yl-1,2,4-triazol-4-yl)-benzoic acid, off-white solid (1.26 g, 33%), MS (ISP) m/z=310.1 [(M+H)+], mp 261° C., was prepared in accordance with the general method of intermediate 2, step B, from commercially available 3-amino-5-bromobenzoic acid (2.70 g, 12.5 mmol) and N-[(E)-dimethylamino-methylideneamino]-2,2-dimethylpropanamide (2.10 g, 13.4 mmol).

Step C

The title compound, off-white foam (0.25 g, 71%), MS (ISP) m/z=365.2 [(M+H)+], mp 198° C., was prepared in accordance with the general method of intermediate 2, step C, from 3-bromo-5-(3-propan-2-yl-1,2,4-triazol-4-yl)-benzoic acid (301 mg, 0.97 mmol) and 2-methyl-propan-2-amine (84.8 mg, 1.16 mmol).

Intermediate 6: 3-Bromo-N-(2-cyclopropylpropan-2-yl)-5-(3-propan-2-yl-1,2,4-triazol-4-yl)-benzamide

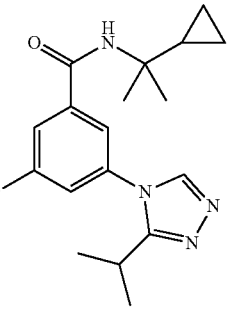

The title compound, off-white foam (0.23 g, 61%), MS (ISP) m/z=393.2 [(M+H)+], mp 137° C., was prepared in accordance with the general method of intermediate 2, step C, from 3-bromo-5-(3-propan-2-yl-1,2,4-triazol-4-yl)-benzoic acid (intermediate 5, step B) (301 mg, 0.97 mmol) and 2-cyclopropylpropan-2-amine hydrochloride (158 mg, 1.16 mmol).

Intermediate 7: 3-Bromo-N-(1-hydroxy-2-methyl-propan-2-yl)-5-(3-propan-2-yl-1,2,4-triazol-4-yl)-benzamide

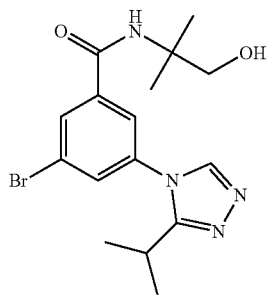 [SMILES: CC(C)c1nncn1-c1cc(Br)cc(C(=O)NC(C)(C)CO)c1]

The title compound, white foam (0.33 g, 90%), MS (ISP) m/z=381.1 [(M+H)⁺], mp 85° C., was prepared in accordance with the general method of intermediate 2, step C, from 3-bromo-5-(3-propan-2-yl-1,2,4-triazol-4-yl)-benzoic acid (intermediate 5, step B) (301 mg, 0.97 mmol) and 2-amino-2-methylpropan-1-ol (103 mg, 1.16 mmol).

Intermediate 8: 3-Bromo-N-(2-methylbutan-2-yl)-5-(3-propan-2-yl-1,2,4-triazol-4-yl)-benzamide

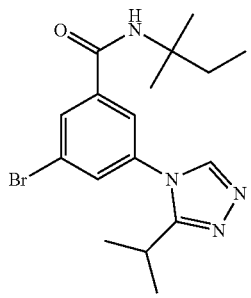 [SMILES: CCC(C)(C)NC(=O)c1cc(Br)cc(-n2cnnc2C(C)C)c1]

The title compound, off-white foam (0.31 g, 85%), MS (ISP) m/z=381.1 [(M+H)⁺], mp 184° C., was prepared in accordance with the general method of intermediate 2, step C, from 3-bromo-5-(3-propan-2-yl-1,2,4-triazol-4-yl)-benzoic acid (intermediate 5, step B) (301 mg, 0.97 mmol) and 2-methylbutan-2-amine (101 mg, 1.16 mmol).

Intermediate 9: 3-(4-Chlorophenyl)-5-[3-(hydroxymethyl)-1,2,4-triazol-4-yl]-benzoic acid

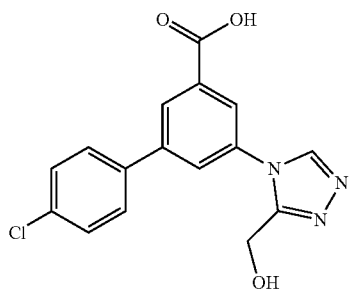 [SMILES: O=C(O)c1cc(-c2ccc(Cl)cc2)cc(-n2cnnc2CO)c1]

Step A

A stirred mixture of commercially available 3-amino-5-bromobenzoic acid (500 mg, 2.31 mmol), toluene (7.6 ml) and 1,1-dimethoxy-N,N-dimethylmethanamine (1.56 g, 1.75 ml, 13.1 mmol was allowed to stir under reflux conditions for 2 h, evaporated and purified by flash chromatography on silica gel [dichloromethane/dichloromethane:methanol 9:1 (0-50%)] to yield methyl 3-bromo-5-[(E)-dimethylaminomethylideneamino]-benzoate (0.65 g, 99%) as a light yellow oil, MS (ISP) m/z=287.1 [(M+H)⁺].

Step B

To a solution of methyl 3-bromo-5-[(E)-dimethylaminomethylideneamino]-benzoate (0.44 g, 1.54 mmol) in acetic acid (772 µl), commercially available 2-hydroxyacetohydrazide (219 mg, 2.31 mmol) was added. The reaction mixture was irradiated in a microwave oven at 160° C. for 15 min in a sealed tube. The reaction mixture was poured into water (30 ml) and extracted with dichloromethane (2×30 ml). The combined organic layers were washed with brine (30 ml), dried (MgSO₄) and evaporated. The crude product (0.51 g) was purified by flash chromatography on silica gel [dichloromethane/dichloromethane:methanol 9:1 (0-50%)] to yield methyl 3-bromo-5-[3-(hydroxymethyl)-1,2,4-triazol-4-yl]-benzoate (0.22 g, 46%) as a white solid, MS (ISP) m/z=314.1 [(M+H)⁺], mp 160° C.

Step C

Methyl 3-(4-chlorophenyl)-5-[3-(hydroxymethyl)-1,2,4-triazol-4-yl]-benzoate, off-white solid (0.14 g, 71%), MS (ISP) m/z=344.2 [(M+H)⁺], mp 203.5° C., was prepared in accordance with the general method of intermediate 1, step B, from methyl 3-bromo-5-[3-(hydroxymethyl)-1,2,4-triazol-4-yl]-benzoate (180 mg, 0.58 mmol) and (4-chlorophenyl)-boronic acid (117 mg, 0.75 mmol).

Step D

A mixture of methyl 3-(4-chlorophenyl)-5-[3-(hydroxymethyl)-1,2,4-triazol-4-yl]-benzoate (130 mg, 378 µmol), THF (628 µl), MeOH (628 µl), water (628 µl) and lithium hydroxide monohydrate (20.6 mg, 491 µmol) was allowed to stir for 3 h at room temperature. The reaction mixture was evaporated to one third, 2N HCl solution (727 ml) was added, the precipitate collected by filtration, washed with water and dried to yield the title compound (0.14 g, %) as a white solid (0.12 g, 96%), MS (ISP) m/z=330.2 [(M+H)⁺], mp 200.5° C.

Intermediate 10:
3-Amino-N-tert-butyl-5-(4-chlorophenyl)-benzamide

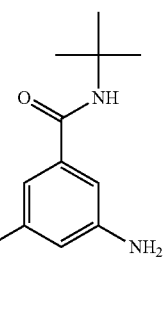

Step A

To a stirred solution of commercially available 3-iodo-5-nitrobenzoic acid (2 g, 6.83 mmol) in THF (49.1 ml) was added at room temperature N,N-diisopropylethylamine (2.21 g, 2.98 ml, 17.1 mmol), 2-methylpropan-2-amine (611 mg, 878 8.19 mmol) and O-(benzotriazol-1-yl)-N,N,N',N'-tetramethyluronium tetrafluoroborate (TBTU) (3.51 g, 10.9 mmol). The reaction mixture was stirred at room temperature for 4 h, evaporated and the residue purified by flash chromatography on silica gel [heptane/ethyl acetate (0-50%)] to yield N-tert-butyl-3-iodo-5-nitrobenzamide (2.31 g, 97%) as an off-white solid, MS (ISP) m/z=349.0 [(M+H)+], mp 166° C.

Step B

A mixture of N-tert-butyl-3-iodo-5-nitrobenzamide (2.3 g, 6.61 mmol) and (4-chlorophenyl)boronic acid (1.34 g, 8.59 mmol) in 1,2-dimethoxyethane (44 ml) and 2M Na₂CO₃ (11 ml, 22 mmol) was purged with argon in an ultrasonic bath for 5 min, triphenylphosphine (347 mg, 1.32 mmol) and palladium(II)acetate (148 mg, 661 μmol) were added and the reaction mixture was stirred for 3 h under reflux conditions. The reaction mixture poured into water (50 ml) and extracted with ethylacetate (2×50 ml). The combined organic layers were washed with brine (40 ml), dried (MgSO₄) and evaporated to give the crude product (3.09 g) as brown solid, which was purified by flash chromatography on silica gel [heptane/ethyl acetate (0-50%)] to yield N-tert-butyl-3-(4-chlorophenyl)-5-nitrobenzamide (2.38 g, 92%) as a brown solid, MS (ISP) m/z=333.1 [(M+H)+], mp 186° C.

Step C

To a stirred solution of N-tert-butyl-3-(4-chlorophenyl)-5-nitrobenzamide (2.38 g, 6.58 mmol) in MeOH (49.8 ml) was added at room temperature tin(II)chloride dihydrate (5.94 g, 26.3 mmol) and the reaction mixture was stirred under reflux conditions for 2 h, evaporated, water (50 ml) and 2N NaOH (50 ml) were added and the mixture was extracted with ethyl acetate (2×75 ml). The combined organic layers were washed with water (50 ml) and brine (50 ml), dried (MgSO₄) and evaporated. The crude product (brown solid, 2.08 g) was purified by flash chromatography on silica gel [dichloromethane/MeOH (1-5%)] to yield the title compound (1.90 g, 95%) as a light brown solid, MS (ISP) m/z=303.1 [(M+H)+], mp 231° C.

EXAMPLE 1

3-(4-Fluorophenyl)-N-(2-methylbutan-2-yl)-5-(1,2,4-triazol-4-yl)-benzamide

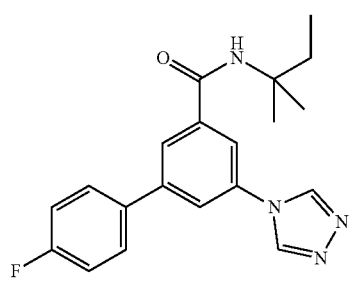 [SMILES: CCC(C)(C)NC(=O)c1cc(-c2ccc(F)cc2)cc(-n2cnnc2)c1]

A stirred mixture of 3-(4-fluorophenyl)-5-(1,2,4-triazol-4-yl)-benzoic acid (intermediate 1) (70.8 mg, 0.25 mmol) and oxalyl chloride (723 mg, 499 μl, 5.7 mmol) was cooled to 0° C., DMF (10 μl) was added, the reaction mixture was allowed to stir for 2 h at room temperature, was evaporated to dryness, THF (2 ml), commercially available 2-methylbutan-2-amine (26.2 mg, 300 μmol) and N,N-diisopropylethylamine (113 mg, 150 μl, 875 μmol) were added and the reaction mixture was allowed to stir room temperature for 17 h. The crude mixture was purified by flash chromatography on silica [dichloromethane/dichloromethane: MeOH 9:1 (20-80%)] and a second time [dichloromethane/dichloromethane: MeOH 9:1 (0-50%)] to yield the title compound as a light yellow solid (29 mg, 33%), MS (ISP) m/z=353.2 [(M+H)+], mp 212° C.

EXAMPLE 2

N-tert-Butyl-3-(4-fluorophenyl)-5-(1,2,4-triazol-4-yl)-benzamide

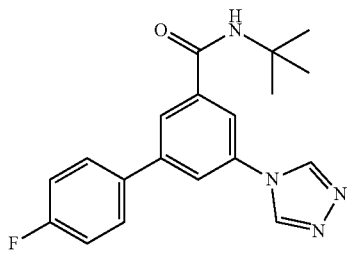 [SMILES: CC(C)(C)NC(=O)c1cc(-c2ccc(F)cc2)cc(-n2cnnc2)c1]

The title compound, light yellow solid (30 mg, 35%), MS (ISP) m/z=339.2 [(M+H)+], mp 204° C., was prepared in accordance with the general method of example 1 from 3-(4-fluorophenyl)-5-(1,2,4-triazol-4-yl)-benzoic acid (intermediate 1) (70.8 mg, 0.25 mmol) and 2-methylbutan-2-amine (21.9 mg, 0.30 mmol).

EXAMPLE 3

N-(2-Cyclopropylpropan-2-yl)-3-(4-fluorophenyl)-5-(1,2,4-triazol-4-yl)-benzamide

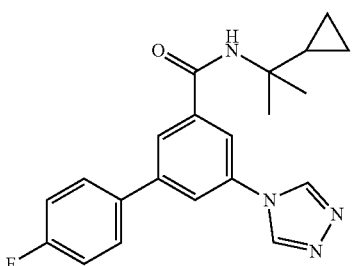

The title compound, light yellow foam (80 mg, 88%), MS (ISP) m/z=365.2 [(M+H)+], mp 135.5° C., was prepared in accordance with the general method of example 1 from 3-(4-fluorophenyl)-5-(1,2,4-triazol-4-yl)-benzoic acid (intermediate 1) (70.8 mg, 0.25 mmol) and 2-cyclopropylpropan-2-amine hydrochloride (40.7 mg, 0.30 mmol).

EXAMPLE 4

3-(4-Fluorophenyl)-5-(1,2,4-triazol-4-yl)-N-(1,1,1-trifluoro-2-methylpropan-2-yl)-benzamide

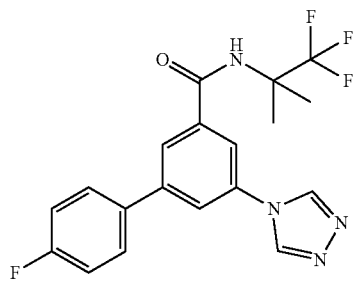

The title compound, white foam (20 mg, 20%), MS (ISP) m/z=393.1 [(M+H)$^+$], mp 147° C., was prepared in accordance with the general method of example 1 from 3-(4-fluorophenyl)-5-(1,2,4-triazol-4-yl)-benzoic acid (intermediate 1) (70.8 mg, 0.25 mmol) and 1,1,1-trifluoro-2-methylpropan-2-amine (38.1 mg, 0.30 mmol).

EXAMPLE 5

N-tert-Butyl-3-(4-fluorophenyl)-5-(3-methyl-1,2,4-triazol-4-yl)-benzamide

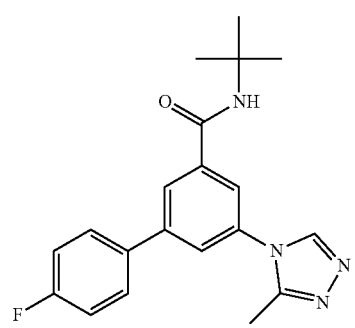 [SMILES: Cc1nncn1-c1cc(C(=O)NC(C)(C)C)cc(-c2ccc(F)cc2)c1]

A mixture of 3-bromo-N-tert-butyl-5-(3-methyl-1,2,4-triazol-4-yl)-benzamide (intermediate 2) (84.3 mg, 0.25 mmol), commercially available (4-fluorophenyl)boronic acid (45.5 mg, 325 μmol), 1,2-dimethoxyethane (1.67 ml) and 2M sodium carbonate solution (416 μl, 833 μmol) was purged with argon in an ultrasonic bath for 5 min, triphenylphosphine (13.1 mg, 50 μmol) and palladium(II)acetate (5.61 mg, 25 μmol) were added, the reaction mixture was stirred for 3 h under reflux conditions, and was evaporated. After filtration the crude reaction mixture was purified by flash chromatography on silica gel [dichloromethane/dichloromethane: MeOH 9:1 (20-100%)] to yield the title compound as a light grey solid (80 mg, 91%), MS (ISP) m/z=353.1 [(M+H)$^+$], mp 235.5° C.

EXAMPLE 6

N-tert-Butyl-3-(4-chlorophenyl)-5-(3-methyl-1,2,4-triazol-4-yl)-benzamide

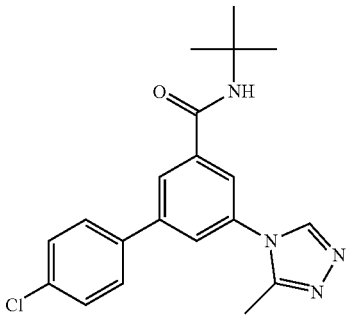 [SMILES: Cc1nncn1-c1cc(C(=O)NC(C)(C)C)cc(-c2ccc(Cl)cc2)c1]

The title compound, off-white solid (90 mg, 98%), MS (ISP) m/z=369.2 [(M+H)$^+$], mp 241° C., was prepared in accordance with the general method of example 5 from 3-bromo-N-tert-butyl-5-(3-methyl-1,2,4-triazol-4-yl)-benzamide (intermediate 2) (84.3 mg, 0.25 mmol) and (4-chlorophenyl)boronic acid (50.8 mg, 325 μmol).

EXAMPLE 7

N-tert-Butyl-3-(3-methyl-1,2,4-triazol-4-yl)-5-[4-(trifluoromethyl)-phenyl]-benzamide

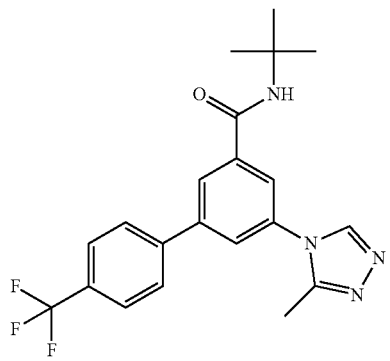 [SMILES: Cc1nncn1-c1cc(C(=O)NC(C)(C)C)cc(-c2ccc(C(F)(F)F)cc2)c1]

The title compound, off-white solid (90 mg, 90%), MS (ISP) m/z=403.2 [(M+H)$^+$], mp 225.5° C., was prepared in accordance with the general method of example 5 from 3-bromo-N-tert-butyl-5-(3-methyl-1,2,4-triazol-4-yl)-benzamide (intermediate 2) (84.3 mg, 0.25 mmol) and (4-trifluoromethyl-phenyl)boronic acid (61.7 mg, 325 μmol).

EXAMPLE 8

N-tert-Butyl-3-(3-tert-butyl-1,2,4-triazol-4-yl)-5-(4-fluorophenyl)-benzamide

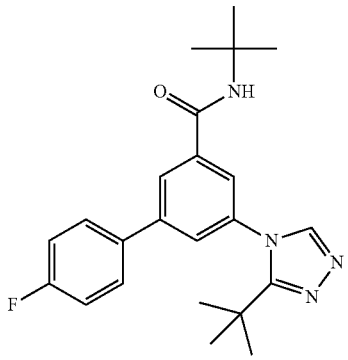 [SMILES: CC(C)(C)NC(=O)c1cc(-c2ccc(F)cc2)cc(-n2cnnc2C(C)(C)C)c1]

The title compound, white solid (98 mg, 99%), MS (ISP) m/z=395.3 [(M+H)⁺], mp 279° C., was prepared in accordance with the general method of example 5 from 3-bromo-N-tert-butyl-5-(3-tert-butyl-1,2,4-triazol-4-yl)-benzamide (intermediate 3) (94.8 mg, 0.25 mmol) and (4-fluorophenyl)boronic acid (45.5 mg, 325 µmol).

EXAMPLE 9

N-tert-Butyl-3-(3-tert-butyl-1,2,4-triazol-4-yl)-5-(4-chlorophenyl)-benzamide

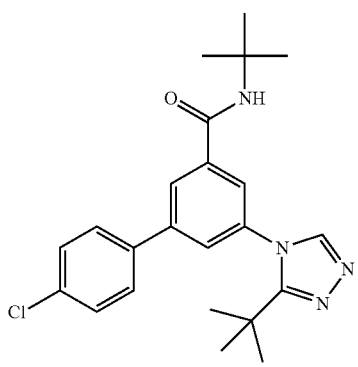 [SMILES: CC(C)(C)NC(=O)c1cc(-c2ccc(Cl)cc2)cc(-n2cnnc2C(C)(C)C)c1]

The title compound, white solid (100 mg, 97%), MS (ISP) m/z=411.2 [(M+H)⁺], mp 292.5° C., was prepared in accordance with the general method of example 5 from 3-bromo-N-tert-butyl-5-(3-tert-butyl-1,2,4-triazol-4-yl)-benzamide (intermediate 3) (94.8 mg, 0.25 mmol) and (4-chlorophenyl)boronic acid (50.8 mg, 325 µmol).

EXAMPLE 10

N-tert-Butyl-3-(3-tert-butyl-1,2,4-triazol-4-yl)-5-[4-(trifluoromethyl)-phenyl]-benzamide

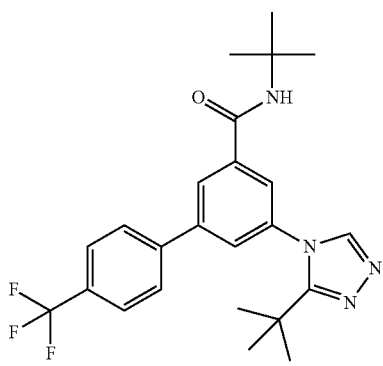 [SMILES: CC(C)(C)NC(=O)c1cc(-c2ccc(C(F)(F)F)cc2)cc(-n2cnnc2C(C)(C)C)c1]

The title compound, white solid (110 mg, 99%), MS (ISP) m/z=445.3 [(M+H)⁺], mp 280.5° C., was prepared in accordance with the general method of example 5 from 3-bromo-N-tert-butyl-5-(3-tert-butyl-1,2,4-triazol-4-yl)-benzamide (intermediate 3) (94.8 mg, 0.25 mmol) and (4-trifluoromethyl-phenyl)boronic acid (61.7 mg, 325 µmol).

EXAMPLE 11

3-(3-tert-Butyl-1,2,4-triazol-4-yl)-N-(2-cyclopropyl-propan-2-yl)-5-[4-(trifluoromethyl)-phenyl]-benzamide

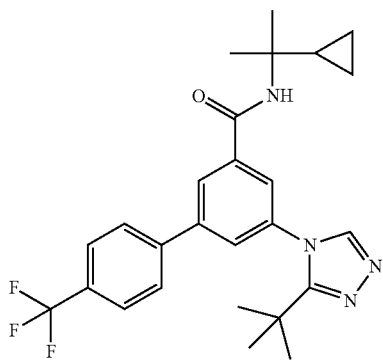 [SMILES: CC(C)(C)c1nncn1-c1cc(C(=O)NC(C)(C)C2CC2)cc(-c2ccc(C(F)(F)F)cc2)c1]

The title compound, white solid (110 mg, 94%), MS (ISP) m/z=471.3 [(M+H)⁺], mp 242.5° C., was prepared in accordance with the general method of example 5 from 3-bromo-5-(3-tert-butyl-1,2,4-triazol-4-yl)-N-(2-cyclopropylpropan-2-yl)-benzamide (intermediate 4) (101 mg, 0.25 mmol) and (4-trifluoromethyl-phenyl)boronic acid (61.7 mg, 325 µmol).

EXAMPLE 12

3-(3-tert-Butyl-1,2,4-triazol-4-yl)-N-(2-cyclopropyl-propan-2-yl)-5-(4-fluorophenyl)-benzamide

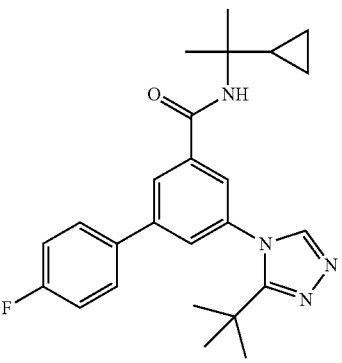 [SMILES: CC(C)(C)c1nncn1-c1cc(C(=O)NC(C)(C)C2CC2)cc(-c2ccc(F)cc2)c1]

The title compound, white foam (90 mg, 86%), MS (ISP) m/z=421.3 [(M+H)⁺], mp 111° C., was prepared in accordance with the general method of example 5 from 3-bromo-5-(3-tert-butyl-1,2,4-triazol-4-yl)-N-(2-cyclopropylpropan-2-yl)-benzamide (intermediate 4) (101 mg, 0.25 mmol) and (4-fluorophenyl)boronic acid (45.5 mg, 325 µmol).

EXAMPLE 13

3-(3-tert-Butyl-1,2,4-triazol-4-yl)-5-(4-chlorophenyl)-N-(2-cyclopropylpropan-2-yl)-benzamide

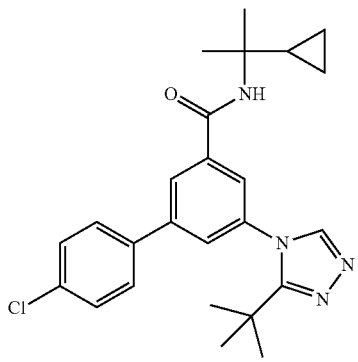 [SMILES: CC(C)(C)c1nncn1-c1cc(C(=O)NC(C)(C)C2CC2)cc(-c2ccc(Cl)cc2)c1]

The title compound, white foam (90 mg, 82%), MS (ISP) m/z=437.3 [(M+H)$^+$], mp 136.5° C., was prepared in accordance with the general method of example 5 from 3-bromo-5-(3-tert-butyl-1,2,4-triazol-4-yl)-N-(2-cyclopropylpropan-2-yl)-benzamide (intermediate 4) (101 mg, 0.25 mmol) and (4-chlorophenyl)boronic acid (50.8 mg, 325 μmol).

EXAMPLE 14

N-tert-Butyl-3-(4-fluorophenyl)-5-(3-propan-2-yl-1,2,4-triazol-4-yl)-benzamide

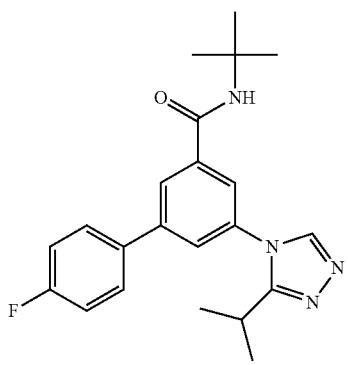 [SMILES: CC(C)c1nncn1-c1cc(C(=O)NC(C)(C)C)cc(-c2ccc(F)cc2)c1]

The title compound, white solid (90 mg, 95%), MS (ISP) m/z=381.2 [(M+H)$^+$], mp 240.5° C., was prepared in accordance with the general method of example 5 from 3-bromo-N-tert-butyl-5-(3-propan-2-yl-1,2,4-triazol-4-yl)-benzamide (intermediate 5) (91.3 mg, 0.25 mmol) and (4-fluorophenyl)boronic acid (45.5 mg, 325 μmol).

EXAMPLE 15

N-tert-Butyl-3-(4-chlorophenyl)-5-(3-propan-2-yl-1,2,4-triazol-4-yl)-benzamide

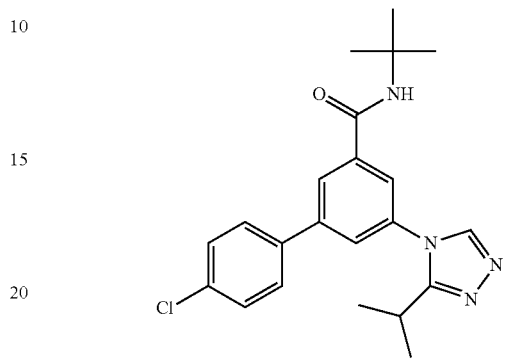

The title compound, white solid (99 mg, 100%), MS (ISP) m/z=397.2 [(M+H)$^+$], mp 239.5° C., was prepared in accordance with the general method of example 5 from 3-bromo-N-tert-butyl-5-(3-propan-2-yl-1,2,4-triazol-4-yl)-benzamide (intermediate 5) (91.3 mg, 0.25 mmol) and (4-chlorophenyl)boronic acid (50.8 mg, 325 μmol).

EXAMPLE 16

N-(2-Cyclopropylpropan-2-yl)-3-(4-fluorophenyl)-5-(3-propan-2-yl-1,2,4-triazol-4-yl)-benzamide The title compound, off-white foam (100 mg, 98%), MS (ISP) m/z=407.3 [(M+H)$^+$], mp 101° C., was prepared in accordance with the general method of example 5 from 3-bromo-N-(2-cyclopropylpropan-2-yl)-5-(3-propan-2-yl-1,2,4-triazol-4-yl)-benzamide (intermediate 6) (97.8 mg, 0.25 mmol) and (4-fluorophenyl)boronic acid (45.5 mg, 325 μmol).

EXAMPLE 17

3-(4-Chlorophenyl)-N-(2-cyclopropyl-propan-2-yl)-5-(3-propan-2-yl-1,2,4-triazol-4-yl)-benzamide

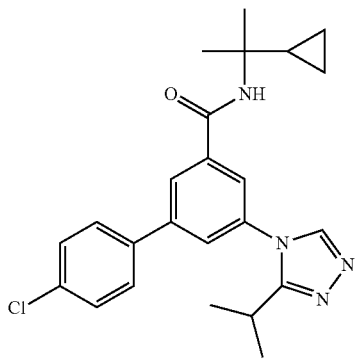 [SMILES: CC(C)c1nncn1-c1cc(C(=O)NC(C)(C)C2CC2)cc(-c2ccc(Cl)cc2)c1]

The title compound, white foam (100 mg, 95%), MS (ISP) m/z=423.3 [(M+H)+], mp 105° C., was prepared in accordance with the general method of example 5 from 3-bromo-N-(2-cyclopropylpropan-2-yl)-5-(3-propan-2-yl-1,2,4-triazol-4-yl)-benzamide (intermediate 6) (97.8 mg, 0.25 mmol) and (4-chlorophenyl)boronic acid (50.8 mg, 325 µmol).

EXAMPLE 18

N-tert-Butyl-3-(3-propan-2-yl-1,2,4-triazol-4-yl)-5-[4-(trifluoromethyl)-phenyl]-benzamide

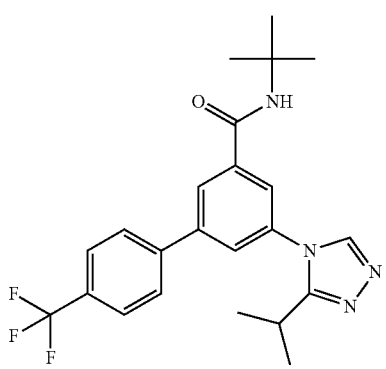 [SMILES: CC(C)c1nncn1-c1cc(C(=O)NC(C)(C)C)cc(-c2ccc(C(F)(F)F)cc2)c1]

The title compound, white foam (70 mg, 99%), MS (ISP) m/z=431.3 [(M+H)+], mp 126° C., was prepared in accordance with the general method of example 5 from 3-bromo-N-tert-butyl-5-(3-propan-2-yl-1,2,4-triazol-4-yl)-benzamide (intermediate 5) (60.0 mg, 164 µmol) and (4-trifluoromethyl-phenyl)boronic acid (40.6 mg, 214 µmol).

EXAMPLE 19

N-(2-Cyclopropyl-propan-2-yl)-3-(3-propan-2-yl-1,2,4-triazol-4-yl)-5-[4-(trifluoromethyl)-phenyl]-benzamide

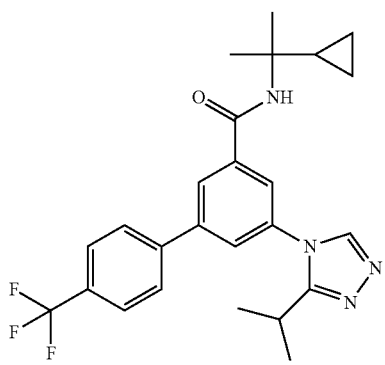 [SMILES: CC(C)c1nncn1-c1cc(C(=O)NC(C)(C)C2CC2)cc(-c2ccc(C(F)(F)F)cc2)c1]

The title compound, white foam (50 mg, 86%), MS (ISP) m/z=457.3 [(M+H)+], mp 100° C., was prepared in accordance with the general method of example 5 from 3-bromo-N-(2-cyclopropylpropan-2-yl)-5-(3-propan-2-yl-1,2,4-triazol-4-yl)-benzamide (intermediate 6) (50.0 mg, 128 µmol) and (4-trifluoromethyl-phenyl)boronic acid (31.5 mg, 166 µmol).

EXAMPLE 20

3-(4-Fluorophenyl)-N-(1-hydroxy-2-methylpropan-2-yl)-5-(3-propan-2-yl-1,2,4-triazol-4-yl)-benzamide

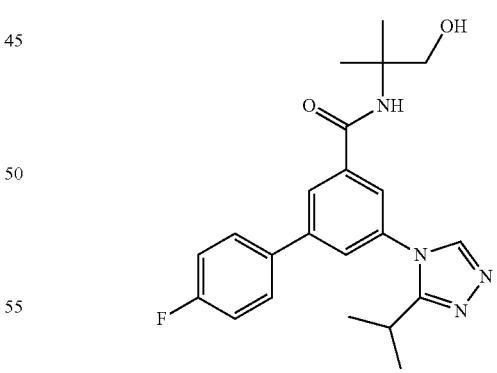

The title compound, white foam (90 mg, 91%), MS (ISP) m/z=397.3 [(M+H)+], mp 171.5° C., was prepared in accordance with the general method of example 5 from 3-bromo-N-(1-hydroxy-2-methylpropan-2-yl)-5-(3-propan-2-yl-1,2,4-triazol-4-yl)-benzamide (intermediate 7) (95.3 mg, 0.25 mmol) and (4-fluorophenyl)boronic acid (45.5 mg, 325 µmol).

EXAMPLE 21

3-(4-Chlorophenyl)-N-(1-hydroxy-2-methylpropan-2-yl)-5-(3-propan-2-yl-1,2,4-triazol-4-yl)-benzamide

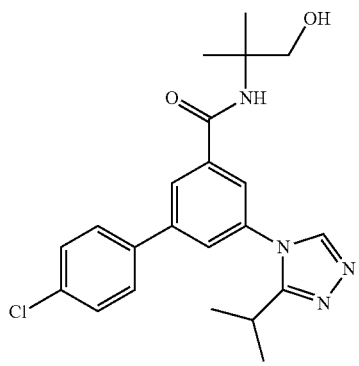 [SMILES: CC(C)c1nncn1-c1cc(C(=O)NC(C)(C)CO)cc(-c2ccc(Cl)cc2)c1]

The title compound, off-white foam (80 mg, 78%), MS (ISP) m/z=413.3 [(M+H)$^+$], mp 180° C., was prepared in accordance with the general method of example 5 from 3-bromo-N-(1-hydroxy-2-methylpropan-2-yl)-5-(3-propan-2-yl-1,2,4-triazol-4-yl)-benzamide (intermediate 7) (95.3 mg, 0.25 mmol) and (4-chlorophenyl)boronic acid (50.8 mg, 325 µmol).

EXAMPLE 22

N-(1-hydroxy-2-methylpropan-2-yl)-3-(3-propan-2-yl-1,2,4-triazol-4-yl)-5-[4-(trifluoromethyl)-phenyl]-benzamide

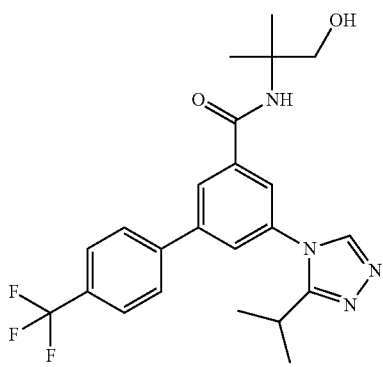 [SMILES: CC(C)c1nncn1-c1cc(C(=O)NC(C)(C)CO)cc(-c2ccc(C(F)(F)F)cc2)c1]

The title compound, light yellow foam (100 mg, 90%), MS (ISP) m/z=447.4 [(M+H)$^+$], mp 214° C., was prepared in accordance with the general method of example 5 from 3-bromo-N-(1-hydroxy-2-methylpropan-2-yl)-5-(3-propan-2-yl-1,2,4-triazol-4-yl)-benzamide (intermediate 7) (95.3 mg, 0.25 mmol) and (4-trifluoromethyl-phenyl)boronic acid (61.7 mg, 325 µmol).

EXAMPLE 23

N-(2-Methylbutan-2-yl)-3-(3-propan-2-yl-1,2,4-triazol-4-yl)-5-[4-(trifluoromethyl)-phenyl]-benzamide

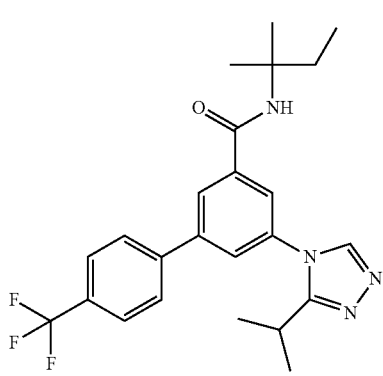 [SMILES: CCC(C)(C)NC(=O)c1cc(-c2ccc(C(F)(F)F)cc2)cc(-n2cnnc2C(C)C)c1]

The title compound, light yellow foam (110 mg, 99%), MS (ISP) m/z=445.4 [(M+H)$^+$], mp 104° C., was prepared in accordance with the general method of example 5 from 3-bromo-N-(2-methylbutan-2-yl)-5-(3-propan-2-yl-1,2,4-triazol-4-yl)-benzamide (intermediate 8) (94.8 mg, 0.25 mmol) and (4-trifluoromethyl-phenyl)boronic acid (61.7 mg, 325 µmol).

EXAMPLE 24

3-(4-Fluorophenyl)-N-(2-methylbutan-2-yl)-5-(3-propan-2-yl-1,2,4-triazol-4-yl)-benzamide

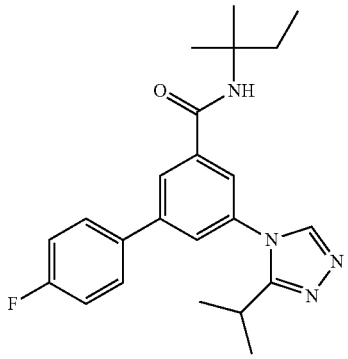 [SMILES: CCC(C)(C)NC(=O)c1cc(-c2ccc(F)cc2)cc(-n2cnnc2C(C)C)c1]

The title compound, off-white foam (98 mg, 99%), MS (ISP) m/z=395.3 [(M+H)$^+$], mp 95° C., was prepared in accordance with the general method of example 5 from 3-bromo-N-(2-methylbutan-2-yl)-5-(3-propan-2-yl-1,2,4-triazol-4-yl)-benzamide (intermediate 8) (94.8 mg, 0.25 mmol) and (4-fluorophenyl)boronic acid (45.5 mg, 325 µmol).

EXAMPLE 25

3-(4-Chlorophenyl)-N-(2-methylbutan-2-yl)-5-(3-propan-2-yl-1,2,4-triazol-4-yl)-benzamide

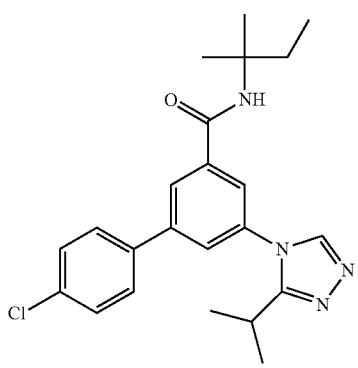 [SMILES: CCC(C)(C)NC(=O)c1cc(-c2ccc(Cl)cc2)cc(-n2cnnc2C(C)C)c1]

The title compound, light yellow foam (100 mg, 97%), MS (ISP) m/z=411.3 [(M+H)⁺], mp 103° C., was prepared in accordance with the general method of example 5 from 3-bromo-N-(2-methylbutan-2-yl)-5-(3-propan-2-yl-1,2,4-triazol-4-yl)-benzamide (intermediate 8) (94.8 mg, 0.25 mmol) and (4-chlorophenyl)boronic acid (50.8 mg, 325 μmol).

EXAMPLE 26

N-tert-Butyl-3-(4-chlorophenyl)-5-[3-(hydroxymethyl)-1,2,4-triazol-4-yl]-benzamide

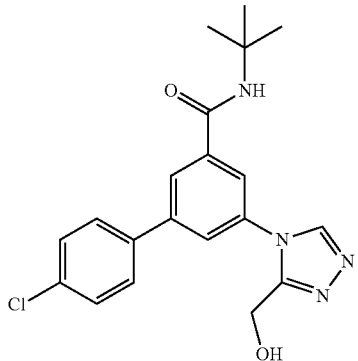 [SMILES: CC(C)(C)NC(=O)c1cc(-c2ccc(Cl)cc2)cc(-n2cnnc2CO)c1]

The title compound, white solid (60 mg, 43%), MS (ISP) m/z=385.3 [(M+H)⁺], mp 210° C., was prepared in accordance with the general method of example 1 from 3-(4-chlorophenyl)-5-[3-(hydroxymethyl)-1,2,4-triazol-4-yl]-benzoic acid (intermediate 9) (120 mg, 0.36 mmol) and 2-methylbutan-2-amine (32.2 mg, 0.44 mmol).

EXAMPLE 27

N-tert-Butyl-3-(4-chlorophenyl)-5-[3-(2-hydroxy-propan-2-yl)-1,2,4-triazol-4-yl]-benzamide

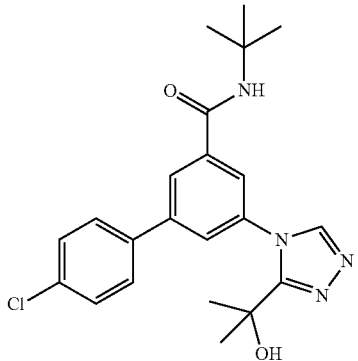 [SMILES: CC(C)(C)NC(=O)c1cc(-c2ccc(Cl)cc2)cc(-n2cnnc2C(C)(C)O)c1]

Step A

A mixture of 3-amino-N-tert-butyl-5-(4-chlorophenyl)-benzamide (intermediate 10) (0.32 g, 1.06 mmol), 1,1-dimethoxy-N,N-dimethylmethanamine (714 mg, 799 μl, 5.99 mmol) and toluene (3.5 ml) was allowed to stir for 2 h under reflux conditions, evaporated and purified by flash chromatography on silica gel [dichloromethane/dichloromethane:methanol 9:1 (0-50%)] to yield N-tert-butyl-3-(4-chlorophenyl)-5-[(E)-dimethylaminomethylideneamino]-benzamide (0.31 g, 82%) as an off-white foam, MS (ISP) m/z=358.3 [(M+H)⁺], mp 79.5° C.

Step B

A mixture of N-tert-butyl-3-(4-chlorophenyl)-5-[(E)-dimethylaminomethylideneamino]-benzamide (0.31 g, 866 mol), commercially available 2-hydroxy-2-methylpropanehydrazide (162 mg, 1.3 mmol, Eq: 1.5) and acetic acid (434 μl) was irradiated in a microwave oven at 140° C. for 15 min in a sealed tube. The mixture was poured into water (10 ml) and extracted with ethyl acetate (3×10 ml). The combined organic layers were washed with brine (15 ml), dried (MgSO₄) and evaporated. The crude product (0.4 g) was purified by flash chromatography on silica gel [dichloromethane/dichloromethane:methanol 9:1 (0-50%)] to yield the title compound (50 mg, 14%) as white foam, MS (ISP) m/z=413.3 [(M+H)⁺], mp 163° C.

EXAMPLE 28

N-tert-Butyl-3-(3,4-difluorophenyl)-5-(3-propan-2-yl-1,2,4-triazol-4-yl)-benzamide

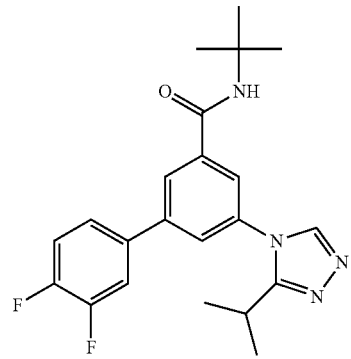 [SMILES: CC(C)c1nncn1-c1cc(C(=O)NC(C)(C)C)cc(-c2ccc(F)c(F)c2)c1]

The title compound, off-white foam (70 mg, 70%), MS (ISP) m/z=399.3 [(M+H)⁺], mp 115° C., was prepared in accordance with the general method of example 5 from 3-bromo-N-tert-butyl-5-(3-propan-2-yl-1,2,4-triazol-4-yl)-benzamide (intermediate 5) (91.3 mg, 250 μmol) and commercially available (3,4-difluoro-phenyl)boronic acid (51.3 mg, 325 μmol).

EXAMPLE 29

N-tert-Butyl-3-(4-methoxyphenyl)-5-(3-propan-2-yl-1,2,4-triazol-4-yl)-benzamide

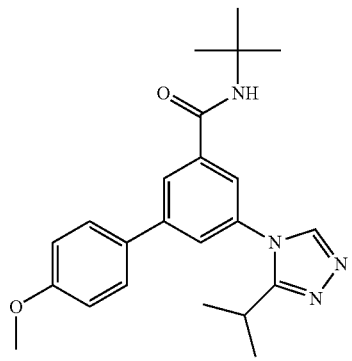 [SMILES: COc1ccc(-c2cc(C(=O)NC(C)(C)C)cc(-n3cnnc3C(C)C)c2)cc1]

The title compound, off-white foam (80 mg, 82%), MS (ISP) m/z=393.3 [(M+H)⁺], mp 107° C., was prepared in accordance with the general method of example 5 from 3-bromo-N-tert-butyl-5-(3-propan-2-yl-1,2,4-triazol-4-yl)-benzamide (intermediate 5) (91.3 mg, 250 μmol) and commercially available (4-methoxy-phenyl)boronic acid (49.4 mg, 325 μmol).

EXAMPLE 30

N-tert-Butyl-3-(4-chloro-3-fluorophenyl)-5-(3-propan-2-yl-1,2,4-triazol-4-yl)-benzamide

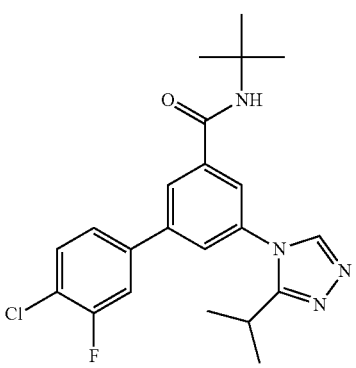 [SMILES: CC(C)c1nncn1-c1cc(C(=O)NC(C)(C)C)cc(-c2ccc(Cl)c(F)c2)c1]

The title compound, white foam (70 mg, 68%), MS (ISP) m/z=415.2 [(M+H)⁺], mp 135° C., was prepared in accordance with the general method of example 5 from 3-bromo-N-tert-butyl-5-(3-propan-2-yl-1,2,4-triazol-4-yl)-benzamide (intermediate 5) (91.3 mg, 250 μmol) and commercially available (4-chloro-3-fluoro-phenyl)boronic acid (56.7 mg, 325 μmol).

EXAMPLE 31

N-tert-Butyl-3-(4-fluoro-3-methyl-phenyl)-5-(3-propan-2-yl-1,2,4-triazol-4-yl)-benzamide

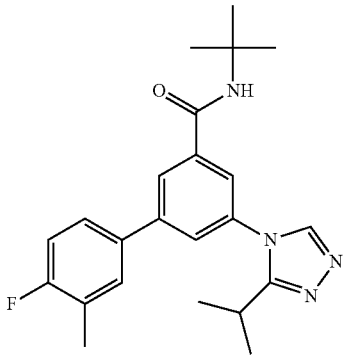 [SMILES: Cc1cc(-c2cc(C(=O)NC(C)(C)C)cc(-n3cnnc3C(C)C)c2)ccc1F]

The title compound, white foam (60 mg, 61%), MS (ISP) m/z=395.3 [(M+H)⁺], mp 106° C., was prepared in accordance with the general method of example 5 from 3-bromo-N-tert-butyl-5-(3-propan-2-yl-1,2,4-triazol-4-yl)-benzamide (intermediate 5) (91.3 mg, 250 μmol) and commercially available (4-fluoro-3-methyl-phenyl)boronic acid (50.0 mg, 325 μmol).

EXAMPLE 32

N-tert-Butyl-3-(3-fluoro-4-methyl-phenyl)-5-(3-propan-2-yl-1,2,4-triazol-4-yl)-benzamide

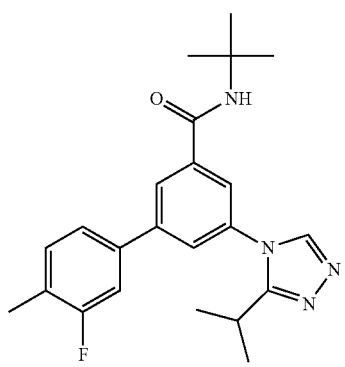 [SMILES: Cc1ccc(-c2cc(C(=O)NC(C)(C)C)cc(-n3cnnc3C(C)C)c2)cc1F]

The title compound, white foam (60 mg, 61%), MS (ISP) m/z=395.4 [(M+H)⁻], mp 109° C., was prepared in accordance with the general method of example 5 from 3-bromo-N-tert-butyl-5-(3-propan-2-yl-1,2,4-triazol-4-yl)-benzamide (intermediate 5) (91.3 mg, 250 μmol) and commercially available (3-fluoro-4-methyl-phenyl)boronic acid (50.0 mg, 325 μmol).

EXAMPLE 33

N-tert-Butyl-3-(4-methyl-phenyl)-5-(3-propan-2-yl-1,2,4-triazol-4-yl)-benzamide

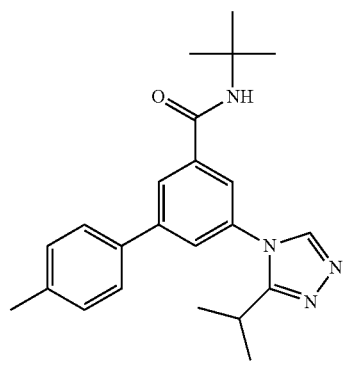 [SMILES: Cc1ccc(-c2cc(C(=O)NC(C)(C)C)cc(-n3cnnc3C(C)C)c2)cc1]

The title compound, off-white foam (60 mg, 64%), MS (ISP) m/z=377.4 [(M+H)⁺], mp 100° C., was prepared in accordance with the general method of example 5 from 3-bromo-N-tert-butyl-5-(3-propan-2-yl-1,2,4-triazol-4-yl)-benzamide (intermediate 5) (91.3 mg, 250 μmol) and commercially available (4-methyl-phenyl)boronic acid (44.2 mg, 325 μmol).

EXAMPLE 34

N-tert-Butyl-3-(4-cyano-phenyl)-5-(3-propan-2-yl-1,2,4-triazol-4-yl)-benzamide

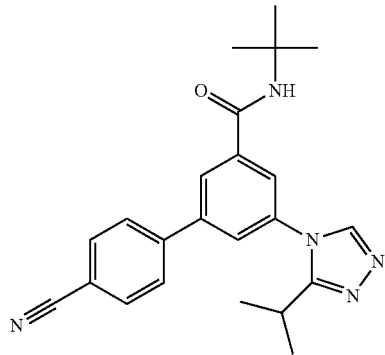 [SMILES: CC(C)c1nncn1-c1cc(C(=O)NC(C)(C)C)cc(-c2ccc(C#N)cc2)c1]

The title compound, off-white solid (50 mg, 52%), MS (ISP) m/z=388.3 [(M+H)⁺], mp 290° C., was prepared in accordance with the general method of example 5 from 3-bromo-N-tert-butyl-5-(3-propan-2-yl-1,2,4-triazol-4-yl)-benzamide (intermediate 5) (91.3 mg, 250 μmol) and commercially available (4-cyano-phenyl)boronic acid (47.8 mg, 325 μmol).

EXAMPLE 35

N-tert-Butyl-3-(4-cyclopropyl-phenyl)-5-(3-propan-2-yl-1,2,4-triazol-4-yl)-benzamide

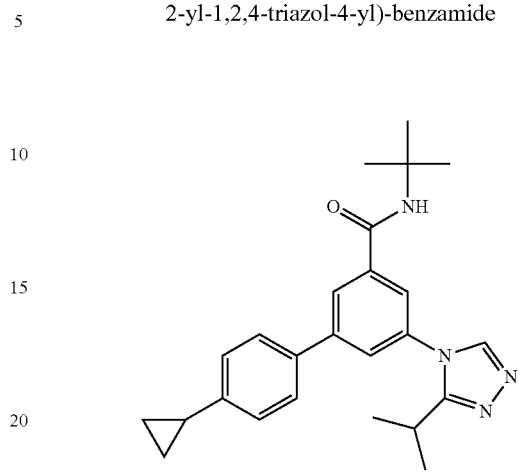

The title compound, off-white foam (40 mg, 40%), MS (ISP) m/z=403.4 [(M+H)⁺], mp 120° C., was prepared in accordance with the general method of example 5 from 3-bromo-N-tert-butyl-5-(3-propan-2-yl-1,2,4-triazol-4-yl)-benzamide (intermediate 5) (91.3 mg, 250 μmol) and commercially available (4-cyclopropyl-phenyl)boronic acid (52.6 mg, 325 μmop.

EXAMPLE 36

(RS)-3-(4-Chlorophenyl)-5-[3-(hydroxymethyl)-1,2,4-triazol-4-yl]-N-(3-methyl-1,1-dioxothiolan-3-yl)-benzamide

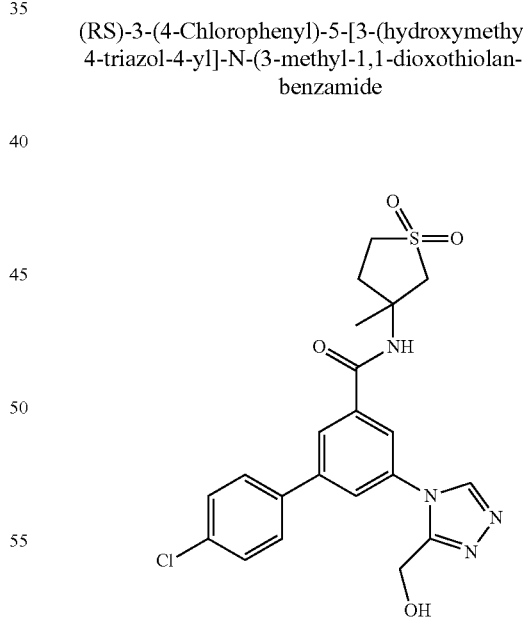

The title compound, white solid (50 mg, 43%), MS (ISP) m/z=461.2 [(M+H)⁺], mp 161.5° C., was prepared in accordance with the general method of example 1 from 3-(4-chlorophenyl)-5-[3-(hydroxymethyl)-1,2,4-triazol-4-yl]-benzoic acid (intermediate 9) (82.4 mg, 0.25 mmol) and commercially available (RS)-3-amino-3-methyltetrahydrothiophene 1,1-dioxide hydrochloride (55.7 mg, 0.30 mmol).

EXAMPLE 37

3-(4-Chlorophenyl)-N-(2-cyclopropyl-propan-2-yl)-5-[3-(hydroxymethyl)-1,2,4-triazol-4-yl]-benzamide

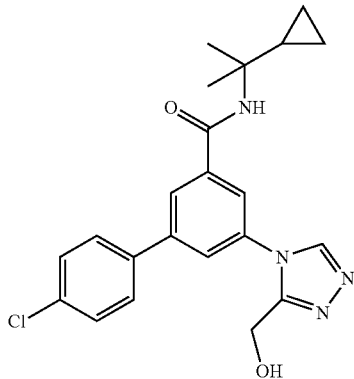 [SMILES: CC(C)(NC(=O)c1cc(-c2ccc(Cl)cc2)cc(-n2cnnc2CO)c1)C1CC1]

The title compound, white foam (70 mg, 56%), MS (ISP) m/z=411.3 [(M+H)⁺], mp 120° C., was prepared in accordance with the general method of example 1 from 3-(4-chlorophenyl)-5-[3-(hydroxymethyl)-1,2,4-triazol-4-yl]-benzoic acid (intermediate 9) (100 mg, 0.30 mmol) and commercially available 2-cyclopropylpropan-2-amine hydrochloride (49.4 mg, 0.36 mmol).

The invention claimed is:

1. A compound of formula I:

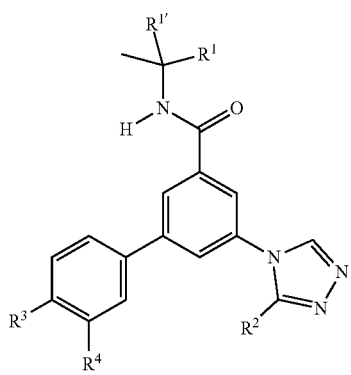

wherein
$R^{1'}$ is $CH_3$
$R^1$ is methyl, ethyl, $CF_3$, $CH_2OH$, cyclopropyl or cyano, or
$R^{1'}$ and $R^1$ may form together a 1,1-dioxo-tetrahydro-thiophen-3-yl ring;
$R^2$ is hydrogen, methyl, ethyl, isopropyl, tert-butyl, cyclopropyl, hydroxmethyl, or 2-propyl-2-ol;
$R^3$ is Cl, F, $CF_3$, cyano, methyl, methoxy, isopropyl, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof.

2. A compound of formula IA according to claim 1,

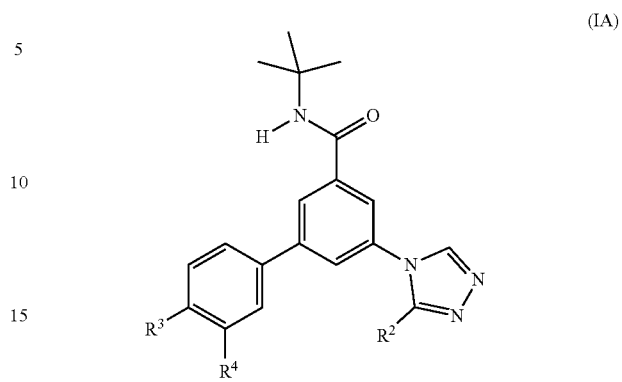

wherein
$R^2$ is hydrogen, methyl, ethyl, isopropyl, tert-butyl, cyclopropyl, hydroxymethyl, or 2-propyl-2-ol;
$R^3$ is Cl, F, $CF_3$, cyano, methyl, methoxy, isopropyl, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof.

3. A compound of formula IA according to claim 2, or a pharmaceutically acceptable salt thereof, wherein the compound is selected from the group consisting of:
N-tert-Butyl-3-(4-fluorophenyl)-5-(1,2,4-triazol-4-yl)-benzamide;
N-tert-Butyl-3-(4-fluorophenyl)-5-(3-methyl-1,2,4-triazol-4-yl)-benzamide;
N-tert-Butyl-3-(4-chlorophenyl)-5-(3-methyl-1,2,4-triazol-4-yl)-benzamide;
N-tert-Butyl-3-(3-methyl-1,2,4-triazol-4-yl)-5[4-(trifluoromethyl)-phenyl]-benzamide;
N-tert-Butyl-3-(3-tert-butyl-1,2,4-triazol-4-yl)-5-(4-fluorophenyl)-benzamide;
N-tert-Butyl-3-(3-tert-butyl-1,2,4-triazol-4-yl)-5-(4-chlorophenyl)-benzamide;
N-tert-Butyl-3-(3-tert-butyl-1,2,4-triazol-4-yl)-5[4-(trifluoromethyl)-phenyl]-benzamide;
N-tert-Butyl-3-(4-fluorophenyl)-5-(3-propan-2-yl-1,2,4-triazol-4-yl)-benzamide;
N-tert-Butyl-3-(4-chlorophenyl)-5-(3-propan-2-yl-1,2,4-triazol-4-yl)-benzamide;
N-tert-Butyl-3-(3-propan-2-yl-1,2,4-triazol-4-yl)-5[4-(trifluoromethyl)-phenyl]-benzamide;
N-tert-Butyl-3-(4-chlorophenyl)-5-[3-(hydroxymethyl)-1,2,4-triazol-4-yl]-benzamide;
N-tert-Butyl-3-(4-chlorophenyl)-5-[3-(2-hydroxypropan-2-yl)-1,2,4-triazol-4-yl]-benzamide;
N-tert-Butyl-3-(3,4-difluorophenyl)-5-(3-propan-2-yl-1,2,4-triazol-4-yl)-benzamide;
N-tert-Butyl-3-(4-methoxyphenyl)-5-(3-propan-2-yl-1,2,4-triazol-4-yl)benzamide;
N-tert-Butyl-3-(4-chloro-3-fluorophenyl)-5-(3-propan-2-yl-1,2,4-triazol-4-yl)-benzamide;
N-tert-Butyl-3-(4-fluoro-3-methyl-phenyl)-5-(3-propan-2-yl-1,2,4-triazol-4-yl)-benzamide;
N-tert-Butyl-3-(3-fluoro-4-methyl-phenyl)-5-(3-propan-2-yl-1,2,4-triazol-4-yl)-benzamide;
N-tert-Butyl-3-(4-methyl-phenyl)-5-(3-propan-2-yl-1,2,4-triazol-4-yl)-benzamide;

N-tert-Butyl-3-(4-cyano-phenyl)-5-(3-propan-2-yl-1,2,4-triazol-4-yl)-benzamide; and N-tert-Butyl-3-(4-cyclopropyl-phenyl)-5-(3-propan-2-yl-1,2,4-triazol-4-yl)-benzamide.

4. A compound of formula IB according to claim 1

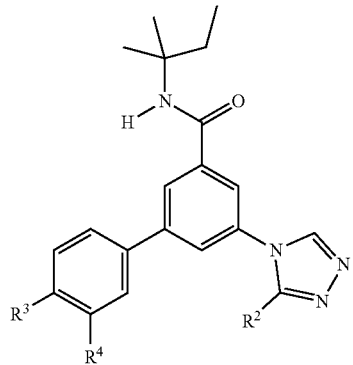

(IB)

wherein
$R^2$ is hydrogen, methyl, ethyl, isopropyl, tert-butyl, cyclopropyl, hydroxmethyl, or 2-propyl-2-ol;
$R^3$ is Cl, F, $CF_3$, cyano, methyl, methoxy, isopropyl, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof.

5. A compound of formula IB according to claim 4, or a pharmaceutically acceptable salt thereof, wherein the compound is selected from the group consisting of
3-(4-Fluorophenyl)-N-(2-methylbutan-2-yl)-5-(1,2,4-triazol-4-yl)-benzamide;
N-(2-Methylbutan-2-yl)-3-(3-propan-2-yl-1,2,4-triazol-4-yl)-5[4-(trifluoromethyl)-phenyl]-benzamide;
3-(4-Fluorophenyl)-N-(2-methylbutan-2-yl)-5-(3-propan-2-yl-1,2,4-triazol-4-yl)-benzamide;
3-(4-Chlorophenyl)-N-(2-methylbutan-2-yl)-5-(3-propan-2-yl-1,2,4-triazol-4-yl)-benzamide.

6. A compound of formula IC according to claim 1

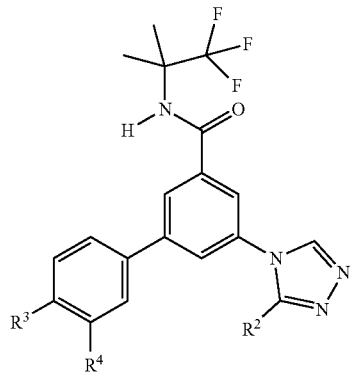

(IC)

wherein
$R^2$ is hydrogen, methyl, ethyl, isopropyl, tert-butyl, cyclopropyl, hydroxmethyl, or 2-propyl-2-ol;
$R^3$ is Cl, F, $CF_3$, cyano, methyl, methoxy, isopropyl, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof.

7. A compound of formula IC according to claim 6, wherein the compound is
3-(4-Fluorophenyl)-5-(1,2,4-triazol-4-yl)-N-(1,1,1-trifluoro-2-methylpropan-2-yl)-benzamide or a pharmaceutically acceptable salt thereof.

8. A compound of formula ID according to claim 1

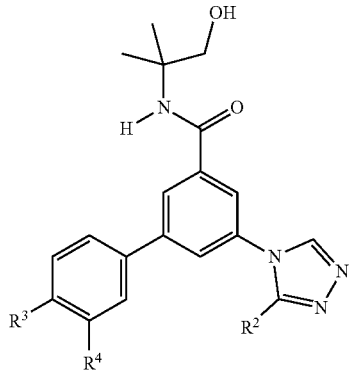

(ID)

wherein
$R^2$ is hydrogen, methyl, ethyl, isopropyl, tert-butyl, cyclopropyl, hydroxmethyl, or 2-propyl-2-ol;
$R^3$ is Cl, F, $CF_3$, cyano, methyl, methoxy, isopropyl, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof.

9. A compound of formula ID according to claim 8, or a pharmaceutically acceptable salt thereof, wherein the compound is
3-(4-Fluorophenyl)-N-(1-hydroxy-2-methylpropan-2-yl)-5-(3-propan-2-yl-1,2,4-triazol-4-yl)-benzamide;
3-(4-Chlorophenyl)-N-(1-hydroxy-2-methylpropan-2-yl)-5-(3-propan-2-yl-1,2,4-triazol-4-yl)-benzamide; or
N-(1-hydroxy-2-methylpropan-2-yl)-3-(3-propan-2-yl-1,2,4-triazol-4-yl)-5[4-(trifluoromethyl)-phenyl]-benzamide.

10. A compound of formula IE according to claim 1

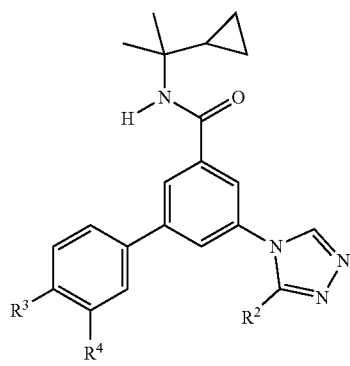

(IE)

wherein
$R^2$ is hydrogen, methyl, ethyl, isopropyl, tert-butyl, cyclopropyl, hydroxmethyl, or 2-propyl-2-ol;

$R^3$ is Cl, F, $CF_3$, cyano, methyl, methoxy, isopropyl, or cyclopropyl;

$R^4$ is hydrogen, methyl, F or Cl;

or a pharmaceutically acceptable salt or acid addition salt, a racemic mixture, or its corresponding enantiomer and/or optical isomer and/or stereoisomer thereof.

11. A compound of formula IE according to claim 10, or a pharmaceutically acceptable salt thereof, wherein the compound is selected from the group consisting of N-(2-Cyclopropylpropan-2-yl)-3-(4-fluorophenyl)-5-(1,2,4-triazol-4-yl)-benzamide;

3-(3-tert-Butyl-1,2,4-triazol-4-yl)-N-(2-cyclopropylpropan-2-yl)-5[4-(trifluoromethyl)-phenyl]-benzamide;

3-(3-tert-Butyl-1,2,4-triazol-4-yl)-N-(2-cyclopropylpropan-2-yl)-5-(4-fluorophenyl)-benzamide;

3-(3-tert-Butyl-1,2,4-triazol-4-yl)-5-(4-chlorophenyl)-N-(2-cyclopropylpropan-2-yl)-benzamide;

N-(2-Cyclopropylpropan-2-yl)-3-(4-fluorophenyl)-5-(3-propan-2-yl-1,2,4-triazol-4-yl)-benzamide;

3-(4-Chlorophenyl)-N-(2-cyclopropyl-propan-2-yl)-5-(3-propan-2-yl-1,2,4-triazol-4-yl)-benzamide;

N-(2-Cyclopropyl-propan-2-yl)-3-(3-propan-2-yl-1,2,4-triazol-4-yl)-5-[4-(trifluoromethyl)-phenyl]-benzamide; and 3-(4-Chlorophenyl)-N-(2-cyclopropyl-propan-2-yl)-5-[3-(hydroxymethyl)-1,2,4-triazol-4-yl]-benzamide.

12. A compound of formula IF according to claim 1

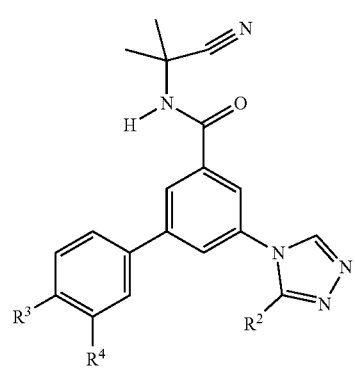

(IF)

wherein $R^2$ is hydrogen, methyl, ethyl, isopropyl, tert-butyl, cyclopropyl, hydroxmethyl, or 2-propyl-2-ol;

$R^3$ is Cl, F, $CF_3$, cyano, methyl, methoxy, isopropyl, or cyclopropyl;

$R^4$ is hydrogen, methyl, F or Cl;

or a pharmaceutically acceptable salt or acid addition salt, a racemic mixture, or its corresponding enantiomer and/or optical isomer and/or stereoisomer thereof.

13. A compound of formula IG according to claim 1

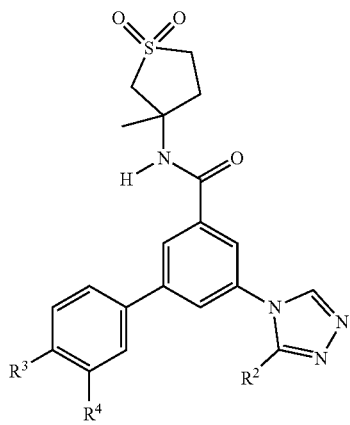

(IG)

$R^2$ is hydrogen, methyl, ethyl, isopropyl, tert-butyl, cyclopropyl, hydroxmethyl, or 2-propyl-2-ol;

$R^3$ is Cl, F, $CF_3$, cyano, methyl, methoxy, isopropyl, or cyclopropyl;

$R^4$ is hydrogen, methyl, F or Cl;

or a pharmaceutically acceptable salt or acid addition salt, a racemic mixture, or its corresponding enantiomer and/or optical isomer and/or stereoisomer thereof.

14. A compound of formula IG according to claim 13, wherein the compound is (RS)-3-(4-Chlorophenyl)-5-[3-(hydroxymethyl)-1,2,4-triazol-4-yl]-N-(3-methyl-1,1-dioxothiolan-3-yl)-benzamide, or a pharmaceutically acceptable salt thereof.

15. A process for the manufacture of a compound of formula I, or a pharmaceutically acceptable salt, as defined in claim 1, which process comprises a) reacting a compound of formula II:

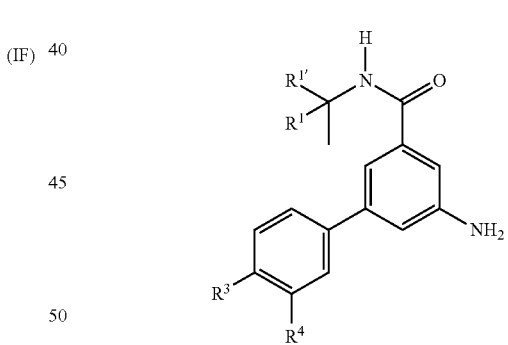

(II)

with N,N-dimethylformamide-dimethylacetal:

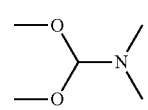

(III)

and a compound of formula

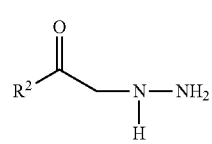

(IV)

to produce a compound of formula I:

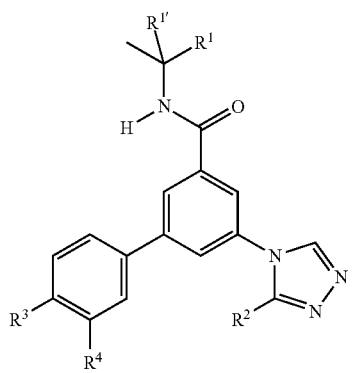

(I)

b) reacting a compound of formula V:

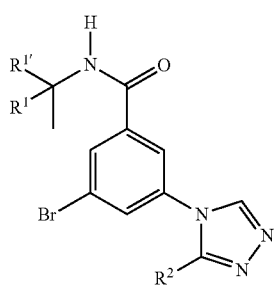

(V)

with a compound of formula IV:

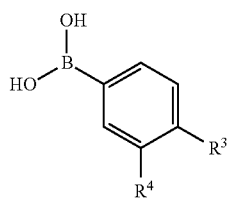

(VI)

to produce a compound of formula I:

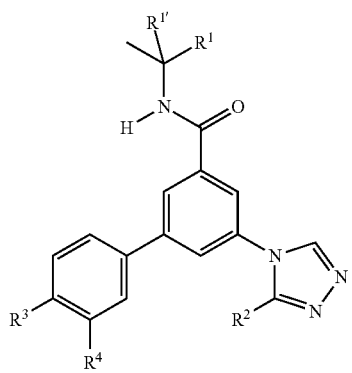

(I)

wherein the substituents are as described above, or if desired, converting the compounds obtained into pharmaceutically acceptable acid addition salts, or c) reacting a compound of formula VII:

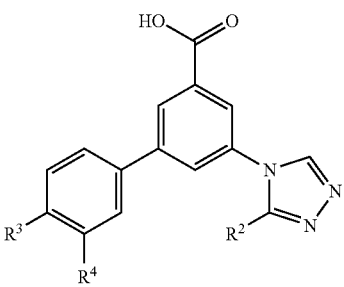

(VII)

with a compound of formula VIII:

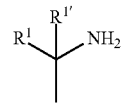

(VIII)

to produce a compound of formula I:

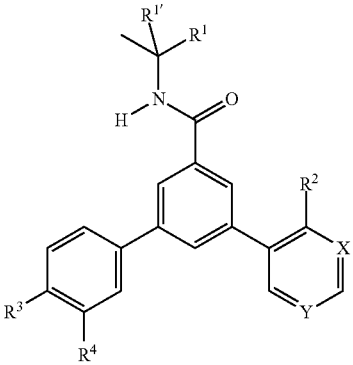

(I)

16. A pharmaceutical composition comprising a compound of formula I as claimed in claim 1 and pharmaceutically acceptable excipients.

17. A method for the treatment of schizophrenia, bipolar disorder, obsessive-compulsive disorder or autism spectrum disorder which method comprises administering an effective amount of a compound of formula I of claim 1, or a pharmaceutically acceptable salt thereof, to a human in need.

* * * * *